US008293978B2

(12) United States Patent
Ohyama

(10) Patent No.: US 8,293,978 B2
(45) Date of Patent: Oct. 23, 2012

(54) MARCHANTIALES-DERIVED UNSATURATED FATTY ACID SYNTHETASE GENES AND USE OF THE SAME

(75) Inventor: Kanji Ohyama, Kanazawa (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 0 days.

(21) Appl. No.: 13/017,228

(22) Filed: Jan. 31, 2011

(65) Prior Publication Data

US 2011/0191906 A1 Aug. 4, 2011

Related U.S. Application Data

(62) Division of application No. 10/584,082, filed as application No. PCT/JP2004/019196 on Dec. 22, 2004, now Pat. No. 7,915,487.

(30) Foreign Application Priority Data

Dec. 22, 2003 (JP) ................................ 2003-425673

(51) Int. Cl.
*A01H 5/00* (2006.01)
*A01H 5/10* (2006.01)
*C12N 15/82* (2006.01)
*C07H 21/04* (2006.01)

(52) U.S. Cl. ..... 800/298; 800/281; 435/419; 435/320.1; 536/23.2

(58) Field of Classification Search .................. None
See application file for complete search history.

(56) References Cited

U.S. PATENT DOCUMENTS 7,714,185 B2 * 5/2010 Napier et al. ................. 800/281

FOREIGN PATENT DOCUMENTS

| JP | 2003-509050 | 3/2003 |
| JP | 2003-523746 | 8/2003 |

OTHER PUBLICATIONS

Thomas Girke et al. "Identification of a novel Δ6-acyl-group desaturase by targeted gene disruption in *Physcomitrella patens*." *The Plant Journal*. 1998, vol. 15, No. 1, pp. 39-48, Blackwell Publishing, U.S.A.
Petra Sperling et al. Abifunctional Δ6-fatty acyl acetylenase/desaturase from the moss *Ceratodon purpureus*. *European Journal of Biochemistry*. 2000, vol. 267, No. 12, pp. 3801-3811, FEBS, U.S.A.
Louise V. Michaelson et al. Isolation of a Δ5-Fatty Acid Desaturase Gene from *Mortierella alpina*. *The Journal of Biological Chemistry*. 1998, vol. 273, No. 30, pp. 19055-19059, American Society for Biochemistry and Molecular Biology, U.S.A.
Shu-Yuan Chiou et al. "Optimizing production of polyunsaturated fatty acids in *Marchantia polymorpha* cell suspension culture." *Journal of Biotechnology*. 2001, vol. 85, No. 3, pp. 247-257, Elsevier, U.S.A.
Yoshifumi Shinmen et al. "Production of arachidonic acid and eicosapentaenoic acids by *Marchantia polymorpha* in cell culture." *Phytochemistry*. 1991, vol. 30, No. 10, pp. 3255-3260, Pergamon Press, Great Britain.
Masataka Kajikawa et al. "Isolation and characterization of Δ6-desaturase, an ELO-like enzyme and Δ5-desaturase from the liverwort *Marchantia polymorpha* and production of arachidonic and eicosapentaenoic acids in the methylotrophic yeast *Pichia pastoris*." *Plant Molecular Biology*. 2004, vol. 54, No. 3, pp. 335-352, Kluwer Academic Publishers, Netherlands.
F. Domergue et al., "Cloning and functional characterization of *Phaeodactylum tricornutum* front-end desaturases involved in eicosapentaenoic acid biosynthesis," Eur. J. Biochem., 2002, vol. 269, pp. 4105-4113.
O. Sayanova et al., "Expression of a borage desaturase cDNA containing an N-terminal cytochrome $b_5$ domain results in the accumulation of high levels of Δ6-desaturated fatty acids in transgenic tobacco," Proc. Natl. Acad. Sci. USA, Apr. 1997, vol. 94, pp. 4211-4216.
F. García-Maroto et al., "Cloning and Molecular Characterization of the Δ6-Desaturase from Two *Echium* Plant Species: Production of GLA by Heterologous Expression in Yeast and Tobacco," Lipids, 2002, vol. 37, No. 4, pp. 417-426.
O. Sayanova et al., "Identification of *Primula* fatty acid Δ6-desaturases with n-3 substrate preferences[1]," FEBS Letters, 2003, vol. 542, pp. 100-104.
H. Whitney et al., "Functional characterisation of two cytochrome $b_5$-fusion desaturases from *Anemone leveillei*: the unexpected identification of a fatty acid Δ6-desaturase," Planta, Jul. 24, 2003, vol. 217, pp. 983-992.
Y. Huang et al., "Cloning of Δ12- and Δ6-Desaturases from *Mortierella alpina* and Recombinant Production of γ-Linolenic Acid in *Saccharomyces cerevisiae*," Lipids, 1999, vol. 34, No. 7, pp. 649-659.
E. Sakuradani et al., "Δ6-Fatty acid desaturase from an arachidonic acid-producing *Mortierella* fungus Gene cloning and its heterologous expression in a fungus, *Aspergillus*," Gene, Aug. 6, 1999, vol. 238, pp. 445-453. J. Napier et al., "Identification of a *Caenorhabditis elegans* Δ6-fatty-acid-desaturase by heterologous expression in *Saccharomyces cerevisiae*," Biochem. J., 1998, vol. 330, pp. 611-614.
A. Reddy et al., "Isolation of a Δ6-desaturase gene from the cyanobacterium *Synechocystis* sp. Strain PCC 6803 by gain-of-function expression in *Anabaena* sp. Strain PCC 7120," Plant Molecular Biology, 1993, vol. 27, pp. 293-300.
T. Aki et al., "Molecular Cloning and Functional Characterization of Rat Δ-6 Fatty Acid Desaturase," Biochemical and Biophysical Research Communications, 1999, vol. 255, No. 3, pp. 575-579.
H. Cho et al., "Cloning, Expression, and Nutritional Regulation of the Mammalian Δ-6 Desaturase," The Journal of Biological Chemistry, Jan. 1, 1999, vol. 274, No. 1, pp. 471-477.
J. Parker-Barnes et al., "Identification and characterization of an enzyme involved in the elongation of n-6 and n-3 polyunsaturated fatty acids," PNAS, Jul. 18, 2000, vol. 97, No. 15, pp. 8284-8289.
F. Beaudoin et al., "Heterologous reconstitution in yeast of the polyunsaturated fatty acid biosynthetic pathway," PNAS, Jun. 6, 2000, vol. 97, No. 12, pp. 6421-6426.
T. Zank et al., "Cloning and functional characterisation of an enzyme involved in the elongation of Δ6-polyunsaturated fatty acids from the moss *Physcomitrella patens*," The Plant Journal, 2002, vol. 31, No. 3, pp. 255-268.
C. Oh et al., "*ELO2* and *ELO3*, Homologues of the *Saccharomyces cerevisiae ELO1* Gene, Function in Fatty Acid Elongation and Are Required for Sphingolipid Formation," The Journal of Biological Chemistry, Jul. 11, 1997, vol. 272, No. 28, pp. 17376-17384.

(Continued)

*Primary Examiner* — Elizabeth McElwain
(74) *Attorney, Agent, or Firm* — Drinker Biddle & Reath LLP

(57) ABSTRACT

A Δ5 fatty acid desaturase gene, a Δ6 fatty acid desaturase gene, and a Δ6 fatty-acid-chain elongase gene are isolated from a single species of Marchantiales. By introducing these genes into higher plants, transformed plants which can produce arachidonic acid and eicosapentaenoic acid (EPA) are obtained.

10 Claims, 1 Drawing Sheet

OTHER PUBLICATIONS

D. James, Jr. et al., "Directed Tagging of the *Arabidopsis Fatty Acid Elongation1* (*FAE1*) Gene with the Maize Transposon *Activator*," The Plant Cell, Mar. 1995, vol. 7, pp. 309-319.

D. Knutzon et al., "Identification of Δ5-Desaturase from *Mortierella alpina* by Heterologous Expression in Bakers' Yeast and Canola," The Journal of Biological Chemistry, Nov. 6, 1998, vol. 273, No. 45, pp. 29360-29366.

L. Michaelson et al., "Functional identification of a fatty acid $\Delta^5$ desaturase gene from *Caenorhabditis elegans*," FEBS Letters, 1998, vol. 439, pp. 215-218.

R. Zolfaghari et al., "Fatty Acid $\Delta^5$-Desaturase mRNA is Regulated by Dietary Vitamin A and Exogenous Retinoic Acid in Liver of Adult Rats[1]," Archives of Biochemistry and Biophysics, Jul. 1, 2001, vol. 391, No. 1, pp. 8-15.

H. Cho et al., "Cloning, Expression, and Fatty Acid Regulation of the Human Δ-5 Desaturase," The Journal of Biological Chemistry, Dec. 24, 1999, vol. 274, No. 52, pp. 37335-37339.

F. Domergue et al., "Acyl Carriers Used as Substrates by the Desaturases and Elongases Involved in Very Long-chain Polyunsaturated Fatty Acids Biosynthesis Reconstituted in Yeast," The Journal of Biological Chemistry, Sep. 12, 2003, vol. 278, No. 37, pp. 35115-35126.

M. Kajikawa et al., "Functional Analysis of a β-Ketoacyl-CoA Synthase Gene, *MpFAE2*, by Gene Silencing in the Liverwort *Marchantia polymorpha* L.," Biosci. Biotechnol. Biochem., 2003, vol. 67, No. 3, pp. 605-612.

M. Kajikawa et al., "*MpFAE3*, a β-Ketoacyl-CoA Synthase Gene in the Liverwort *Marchantia polymorpha* L., is Preferentially Involved in Elongation of Palmitic Acid to Stearic Acid," Biosci. Biotechnol. Biochem., 2003, vol. 67, No. 8, pp. 1667-1674.

V. Dembitsky, "Lipids of Bryophytes," Prog. Lipid Res., 1993, vol. 32, No. 3, pp. 281-356.

T. Hashimoto-Gotoh et al., "An oligodeoxyribonucleotide-directed dual amber method for site-directed utagenesis," Gene, 1995, vol. 152, pp. 271-275.

L. Zhang et al., "Gene Expression Profiles in Normal and Cancer Cells," Science, May 23, 1997, vol. 276, pp. 1268-1272.

V. Velculescu et al., "Characterization of the Yeast Transcriptome," Cell, Jan. 24, 1997, vol. 88, pp. 243-251.

V. Velculescu et al., "Serial Analysis of Gene Expression," Science, Oct. 20, 1995, vol. 270, pp. 484-487.

K. Polyak et al., "A model for p53-induced apoptosis," Nature, Sep. 18, 1997, vol. 389, pp. 300-305.

M. Fujisawa et al., "Isolation of X and Y Chromosome-Specific DNA Markers from a Liverwort, *Marchantia polymorpha*, by Representational Difference Analysis," Genetics, Nov. 2001, vol. 159, pp. 981-985.

D. Mitsuhara et al., "Efficient Promoter Cassettes for Enhanced Expression of Foreign Genes in Dicotyledonous and Monocotyledonous Plants," Plant Cell Physiol., 1996, vol. 37, No. 1, pp. 49-59.

F. Van Engelen et al., "pBINPLUS: an improved plant transformation vector based on pBIN19," Transgenic Research, 1995, vol. 4, pp. 288-290.

Y. Tanaka et al., "Molecular Cloning and Characterization of *Rosa hybrida* Dihydroflavonol 4-reductase Gene," Plant Cell Physiol., 1995, vol. 36, No. 6, pp. 1023-1031.

F. Brugliera et al., "Isolation and characterization of a cDNA clone corresponding to the *Rt* locus of *Petunia hybrida*," The Plant Journal, 1994, vol. 5, No. 1, pp. 81-92.

G. Lazo et al., "A DNA Transformation-Competent *Arabidopsis* Genomic Library in *Agrobacterium*," Bio/Technology, Oct. 1991, vol. 9, pp. 963-967.

A. Abbadi et al., "Biosynthesis of Very-Long-Chain Polyunsaturated Fatty Acids in Transgenic Oilseeds: Constraints on Their Accumulation," The Plant Cell, Oct. 2004, vol. 16, pp. 2734-2748.

B. Qi et al., "Production of very long chain polyunsaturated omega-3 and omega-6 fatty acids in plants," Nature Biotechnology, Jun. 2004, vol. 22, No. 6, pp. 739-745.

International Search Report issued on Dec. 4, 2005 in International PCT Application PCT/JP2004/019196 filed Dec. 22, 2004.

Takenaka et al., "Direct transformation and plant regeneration of the haploid liverwort *Marchantia polymorpha* L.," Transgenic Research 9, pp. 179-185, 2000, Kluwer Academic Publishers, Netherlands.

International Search Report mailed Apr. 12, 2005, in International PCT Application No. PCT/JP2004/019196 filed Dec. 22, 2004.

Kajikawa et al., "Functional Analysis of a β-Ketoacyl-CoA Synthase Gene, *MpFAE2*, by Gene Silencing in the Liverwort *Marchantia polymorpha* L.," Biosci. Biotechnol. Biochem. 67(3), 605-612, 2003, pp. 605-612.

Matsui et al., "Developmental Changes of Lipoxygenase and Fatty Acid Hydroperoxide Lyase Activities in Cultured Cells of *Marchantia polymorpha*," Phytochemistry, vol. 41, No. 1, 1996, pp. 177-182, Pergamon, New York.

European Search Report issued Apr. 4, 2008, in European Application No. EP 04 80 7553.

European Search Report issued Jun. 1, 2010, in European Application No. EP 10 15 7466.

European Search Report issued Jun. 4, 2010, in European Application No. EP 10 15 7464.

Kajikawa et al, Plant Molecular Biology 54(3): 335-352, 2004.

Sequence alignment of SEQ ID No: 1 to Sequence Accession AY583463, Kajikawa et al, Aug. 4, 2007.

Y. Fujino, "Introduction to Lipid Analysis Method, Biochemical Experimental Method 9," Gakkai Shuppan Center, 1978, pp. 42-46, pp. 154-157, and its Partial English-language translation.

A. Yamada, "Experimental Method for Plant Lipid Metabolism, Biochemical Experimental Method 24," Gakkai Shuppan Center, 1989, pp. 2-9, and its partial English-language translation.

* cited by examiner

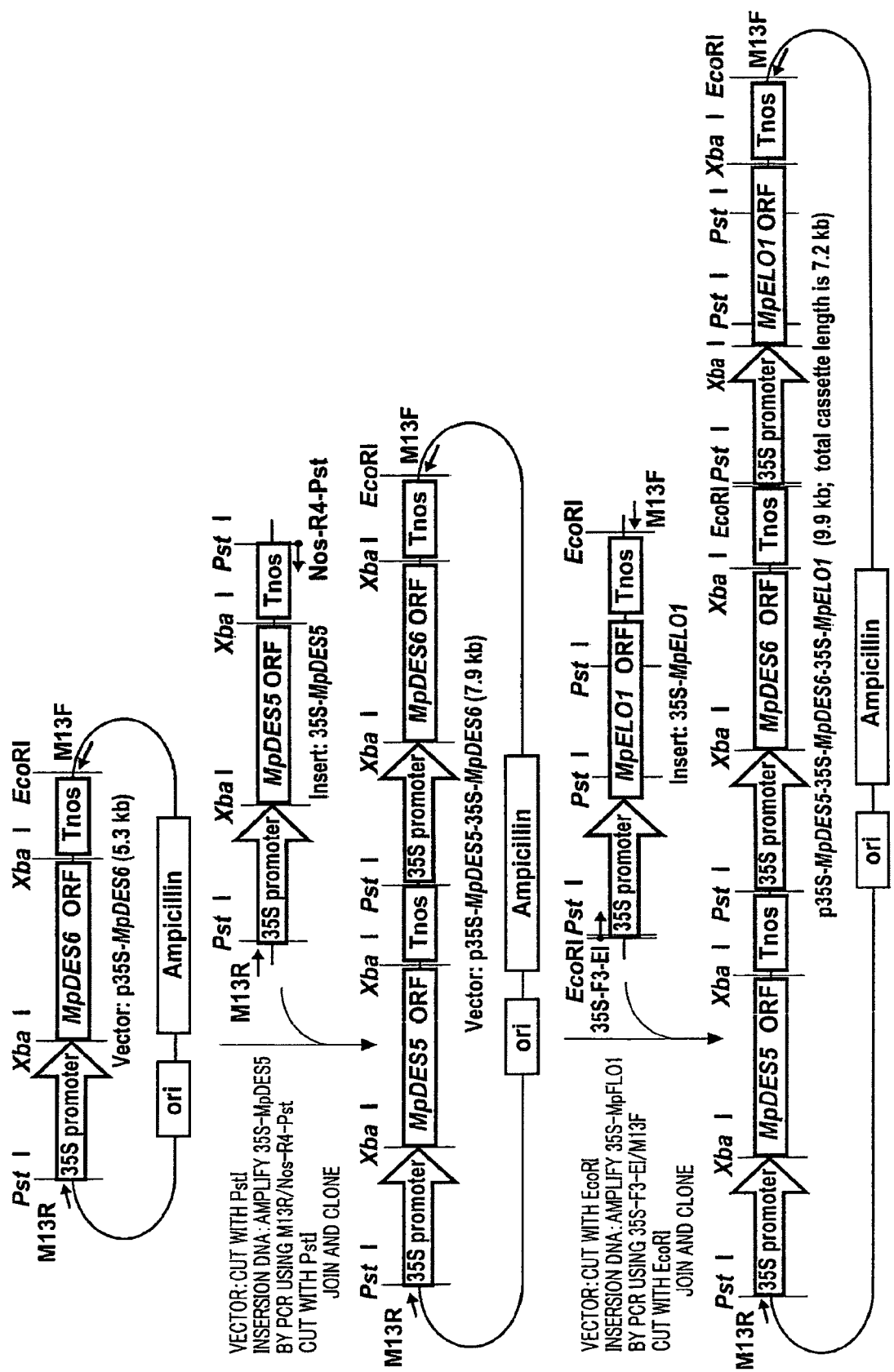

SEQUENCE LISTING

```
<160> NUMBER OF SEQ ID NOS: 46

<210> SEQ ID NO 1
<211> LENGTH: 2519
<212> TYPE: DNA
<213> ORGANISM: Marchantia polymorpha
<220> FEATURE:
```

<221> NAME/KEY: CDS
<222> LOCATION: (253)..(1698)

<400> SEQUENCE: 1

```
atagatccaa tttcataagt cgacgagaaa ggcagaaggc gagaagcggc aggcagcgag      60
cgcgagcgcc agagctcttg ctcccctcgc tcatcgctcg cattgccgca ttttgtgagt     120
gtcggactga tcactcagtc cgtcactgca aacgcgagcg agcgagagtg cgagtgagcg     180
agcgagcgag cgagagccgc ggtgtgtctg tgagatccaa tcctttttct gctttgcgcg     240
ctgtggggcg cg atg gcc tcg tcc acc acc acc gcc gtg aag caa tct tcg    291
              Met Ala Ser Ser Thr Thr Thr Ala Val Lys Gln Ser Ser
                1               5                  10 ggt ggg ctg tgg tcg aaa tgg ggc acc ggc agc aac ttg agc ttc gtg      339
Gly Gly Leu Trp Ser Lys Trp Gly Thr Gly Ser Asn Leu Ser Phe Val
 15                  20                  25 tcg cgc aag gag cag cag cag cag cag cag agc tct ccc gag gcg          387
Ser Arg Lys Glu Gln Gln Gln Gln Gln Gln Ser Ser Pro Glu Ala
 30                  35                  40                  45 tcg act ccc gcg gcg cag cag gag aaa tcc atc agt aga gaa tcc atc      435
Ser Thr Pro Ala Ala Gln Gln Glu Lys Ser Ile Ser Arg Glu Ser Ile
                 50                  55                  60 ccc gag ggc ttc ttg acc gtg gag gag gtg tcg aag cac gac aat ccg      483
Pro Glu Gly Phe Leu Thr Val Glu Glu Val Ser Lys His Asp Asn Pro
                 65                  70                  75 agc gac tgc tgg atc gtc atc aac gac aag gtg tac gac gtg agc gca      531
Ser Asp Cys Trp Ile Val Ile Asn Asp Lys Val Tyr Asp Val Ser Ala
 80                  85                  90 ttc ggg aag acg cat ccg ggc ggc cct gtg atc ttc acg cag gcc ggc      579
Phe Gly Lys Thr His Pro Gly Gly Pro Val Ile Phe Thr Gln Ala Gly
 95                 100                 105 cgc gac gcc acg gat tct ttc aag gtt ttc cac tcc gcc aag gcg tgg      627
Arg Asp Ala Thr Asp Ser Phe Lys Val Phe His Ser Ala Lys Ala Trp
110                 115                 120                 125 cag ttt ctc cag gac ctg tac atc gga gat ctg tac aat gcc gag cca      675
Gln Phe Leu Gln Asp Leu Tyr Ile Gly Asp Leu Tyr Asn Ala Glu Pro
                130                 135                 140 gtg tcg gag ctg gtg aag gat tac cga gac ctg agg acg gcg ttc atg      723
Val Ser Glu Leu Val Lys Asp Tyr Arg Asp Leu Arg Thr Ala Phe Met
                145                 150                 155 cgt tct cag cta ttc aag agc agt aaa atg tac tac gtg acc aag tgc      771
Arg Ser Gln Leu Phe Lys Ser Ser Lys Met Tyr Tyr Val Thr Lys Cys
                160                 165                 170 gtc aca aat ttt gca att ctt gcc gcc agt ctc gca gtc atc gcg tgg      819
Val Thr Asn Phe Ala Ile Leu Ala Ala Ser Leu Ala Val Ile Ala Trp
175                 180                 185 agc cag acg tat ctg gcg gtt ttg tgc tcc agt ttc ctg ttg gct ctc      867
Ser Gln Thr Tyr Leu Ala Val Leu Cys Ser Ser Phe Leu Leu Ala Leu
190                 195                 200                 205 ttc tgg cag caa tgt gga tgg tta tcg cac gat ttt ctc cac cac cag      915
Phe Trp Gln Gln Cys Gly Trp Leu Ser His Asp Phe Leu His His Gln
                210                 215                 220 gtg acc gag aac cga tcg ctc aac acg tac ttc ggc ggc ctg ttc tgg      963
Val Thr Glu Asn Arg Ser Leu Asn Thr Tyr Phe Gly Gly Leu Phe Trp
                225                 230                 235 ggt aac ttc gcc cag ggc tac agc gtg gga tgg tgg aag acc aag cac     1011
Gly Asn Phe Ala Gln Gly Tyr Ser Val Gly Trp Trp Lys Thr Lys His
                240                 245                 250 aat gtg cac cac gcg gcc acg aac gaa tgc gac gac aag tat cag ccc     1059
Asn Val His His Ala Ala Thr Asn Glu Cys Asp Asp Lys Tyr Gln Pro
255                 260                 265
```

| | | |
|---|---|---|
| atc gat ccc gac atc gac acc gtg ccc ctg ctc gcc tgg agc aag gaa<br>Ile Asp Pro Asp Ile Asp Thr Val Pro Leu Leu Ala Trp Ser Lys Glu<br>270                       275                     280                     285 | 1107 |
| atc ttg gcc acc gtc gac gac caa ttc ttc cga tcg atc atc agc gtg<br>Ile Leu Ala Thr Val Asp Asp Gln Phe Phe Arg Ser Ile Ile Ser Val<br>                     290                     295                     300 | 1155 |
| cag cac ctt ctg ttc ttc ccg ctc ctc ttc ttg gca aga ttc agc tgg<br>Gln His Leu Leu Phe Phe Pro Leu Leu Phe Leu Ala Arg Phe Ser Trp<br>               305                          310                    315 | 1203 |
| ctg cat tcg agt tgg gcc cac gcc agc aac ttc gag atg cct cgg tac<br>Leu His Ser Ser Trp Ala His Ala Ser Asn Phe Glu Met Pro Arg Tyr<br>       320                     325                     330 | 1251 |
| atg aga tgg gcg gag aag gcc tcg ctc ctc ggg cac tac ggc gcc tca<br>Met Arg Trp Ala Glu Lys Ala Ser Leu Leu Gly His Tyr Gly Ala Ser<br>335                       340                     345 | 1299 |
| atc ggc gcc gcc ttc tac att ttg ccc atc ccc cag gcc atc tgc tgg<br>Ile Gly Ala Ala Phe Tyr Ile Leu Pro Ile Pro Gln Ala Ile Cys Trp<br>350                       355                     360                    365 | 1347 |
| ctc ttc ttg tcg caa ctg ttt tgc ggc gct ctc agc att gtc ttc<br>Leu Phe Leu Ser Gln Leu Phe Cys Gly Ala Leu Leu Ser Ile Val Phe<br>               370                          375                    380 | 1395 |
| gtg atc agc cac aat ggc atg gat gtg tac aac gac ccc cgg gac ttc<br>Val Ile Ser His Asn Gly Met Asp Val Tyr Asn Asp Pro Arg Asp Phe<br>               385                          390                    395 | 1443 |
| gtg acg gcc caa gtc acc tcg acc aga aac atc gaa ggc aac ttc ttc<br>Val Thr Ala Gln Val Thr Ser Thr Arg Asn Ile Glu Gly Asn Phe Phe<br>             400                     405                    410 | 1491 |
| aac gac tgg ttc acc gga ggc ctg aac agg cag att gag cac cat ctg<br>Asn Asp Trp Phe Thr Gly Gly Leu Asn Arg Gln Ile Glu His His Leu<br>       415                     420                     425 | 1539 |
| ttt ccg tct ctt ccg agg cac aac ctc gcc aag gtc gcg cca cac gtc<br>Phe Pro Ser Leu Pro Arg His Asn Leu Ala Lys Val Ala Pro His Val<br>430                       435                     440                    445 | 1587 |
| aag gcg ctc tgc gcc aag cac ggt ttg cat tac gaa gaa ttg agt ctg<br>Lys Ala Leu Cys Ala Lys His Gly Leu His Tyr Glu Glu Leu Ser Leu<br>               450                          455                    460 | 1635 |
| ggc acg gga gtc tgt cgt gtc ttc aat cgg cta gta gag gta gca tac<br>Gly Thr Gly Val Cys Arg Val Phe Asn Arg Leu Val Glu Val Ala Tyr<br>       465                     470                     475 | 1683 |
| gct gcg aaa gta tag atcgacgaga gtttcccacc aacacagtta gaacaaggga<br>Ala Ala Lys Val<br>480 | 1738 |
| atagtacgag agaaggagac agcaacctgg acttttttgtt cctgatgttg catactttct | 1798 |
| cgaatatacg tctccacgcc ttcaagtttc agcttcaact gattgtcttc agtaaccatc | 1858 |
| gcttgctcca actgggcgac ctgcagaatt gaagatcagt tttactgagt ttgtaccgag | 1918 |
| agtttcccaa attttgttgt aggctgatga cccaatccta gcatacactt taggaataag | 1978 |
| cagtctcaac ataattaggt ccatcattca gcaatttcga tacagcgcct gggattcgac | 2038 |
| gagtttacac gatgagtatg gcttgtaact ggccttctca aggtagcctt ggatctcccc | 2098 |
| gggcctcttg ccatcccatt cacccaatcg agattctgca gtctccaacc ttttctggaa | 2158 |
| gttctcaatc tgtaacctct gttgtagaga tagcatacgc cacaagacaa ggtctttgtg | 2218 |
| aacacagtcg tctaacaaac agcaagttgt gtggattggc atctaaataa ccgcctctgg | 2278 |
| tcaagtaaca gcaggtgttc cgcagtttcc aggaacatac tttgtttctg tcacagccag | 2338 |
| gcggtgaata gtaaagccaa ttcaacacat acgggagaag atgggtcgat atttgtattt | 2398 |
| ggcagggtgt ccagatttca cccatcagtc tctcacttgc ttgtatgtcc ctgacgtgct | 2458 |

-continued

```
tcaaaatttt gcgcggggaa tcatcaatat acttaccatt tgtaaaaaaa aaaaaaaaa    2518 a                                                                   2519
```

<210> SEQ ID NO 2
<211> LENGTH: 481
<212> TYPE: PRT
<213> ORGANISM: Marchantia polymorpha

<400> SEQUENCE: 2

```
Met Ala Ser Ser Thr Thr Thr Ala Val Lys Gln Ser Ser Gly Gly Leu
  1               5                  10                  15

Trp Ser Lys Trp Gly Thr Gly Ser Asn Leu Ser Phe Val Ser Arg Lys
                 20                  25                  30

Glu Gln Gln Gln Gln Gln Gln Ser Ser Pro Glu Ala Ser Thr Pro
             35                  40                  45

Ala Ala Gln Gln Glu Lys Ser Ile Ser Arg Glu Ser Ile Pro Glu Gly
         50                  55                  60

Phe Leu Thr Val Glu Glu Val Ser Lys His Asp Asn Pro Ser Asp Cys
 65                  70                  75                  80

Trp Ile Val Ile Asn Asp Lys Val Tyr Asp Val Ser Ala Phe Gly Lys
                 85                  90                  95

Thr His Pro Gly Gly Pro Val Ile Phe Thr Gln Ala Gly Arg Asp Ala
            100                 105                 110

Thr Asp Ser Phe Lys Val Phe His Ser Ala Lys Ala Trp Gln Phe Leu
        115                 120                 125

Gln Asp Leu Tyr Ile Gly Asp Leu Tyr Asn Ala Glu Pro Val Ser Glu
    130                 135                 140

Leu Val Lys Asp Tyr Arg Asp Leu Arg Thr Ala Phe Met Arg Ser Gln
145                 150                 155                 160

Leu Phe Lys Ser Ser Lys Met Tyr Tyr Val Thr Lys Cys Val Thr Asn
                165                 170                 175

Phe Ala Ile Leu Ala Ala Ser Leu Ala Val Ile Ala Trp Ser Gln Thr
            180                 185                 190

Tyr Leu Ala Val Leu Cys Ser Ser Phe Leu Leu Ala Leu Phe Trp Gln
        195                 200                 205

Gln Cys Gly Trp Leu Ser His Asp Phe Leu His Gln Val Thr Glu
    210                 215                 220

Asn Arg Ser Leu Asn Thr Tyr Phe Gly Gly Leu Phe Trp Gly Asn Phe
225                 230                 235                 240

Ala Gln Gly Tyr Ser Val Gly Trp Trp Lys Thr Lys His Asn Val His
                245                 250                 255

His Ala Ala Thr Asn Glu Cys Asp Asp Lys Tyr Gln Pro Ile Asp Pro
            260                 265                 270

Asp Ile Asp Thr Val Pro Leu Leu Ala Trp Ser Lys Glu Ile Leu Ala
        275                 280                 285

Thr Val Asp Asp Gln Phe Phe Arg Ser Ile Ile Ser Val Gln His Leu
    290                 295                 300

Leu Phe Phe Pro Leu Leu Phe Leu Ala Arg Phe Ser Trp Leu His Ser
305                 310                 315                 320

Ser Trp Ala His Ala Ser Asn Phe Glu Met Pro Arg Tyr Met Arg Trp
                325                 330                 335

Ala Glu Lys Ala Ser Leu Leu Gly His Tyr Gly Ala Ser Ile Gly Ala
            340                 345                 350

Ala Phe Tyr Ile Leu Pro Ile Pro Gln Ala Ile Cys Trp Leu Phe Leu
```

```
                    355                 360                 365
Ser Gln Leu Phe Cys Gly Ala Leu Leu Ser Ile Val Phe Val Ile Ser
    370                 375                 380

His Asn Gly Met Asp Val Tyr Asn Asp Pro Arg Asp Phe Val Thr Ala
385                 390                 395                 400

Gln Val Thr Ser Thr Arg Asn Ile Glu Gly Asn Phe Phe Asn Asp Trp
                405                 410                 415

Phe Thr Gly Gly Leu Asn Arg Gln Ile Glu His His Leu Phe Pro Ser
                420                 425                 430

Leu Pro Arg His Asn Leu Ala Lys Val Ala Pro His Val Lys Ala Leu
            435                 440                 445

Cys Ala Lys His Gly Leu His Tyr Glu Glu Leu Ser Leu Gly Thr Gly
    450                 455                 460

Val Cys Arg Val Phe Asn Arg Leu Val Glu Val Ala Tyr Ala Ala Lys
465                 470                 475                 480

Val
```

<210> SEQ ID NO 3
<211> LENGTH: 1577
<212> TYPE: DNA
<213> ORGANISM: Marchantia polymorpha
<220> FEATURE:
<221> NAME/KEY: CDS
<222> LOCATION: (194)..(1066)

<400> SEQUENCE: 3

```
ctcaacgctc tctctcgccc gccctctgtc ttccgctgcg ccttcttctc ggcgcctctt      60
tctgtcgaga ggagcggcag ctgcagctct cgagagaggg gagcaggacg agagcgaggg    120
cgaatccgcc gagagtcgat cgggattggg tagaaggagg agaaggagga gaagaggagg    180
aggaggagca gcg atg gag gcg tac gag atg gtg gat agt ttt gtg tcg      229
            Met Glu Ala Tyr Glu Met Val Asp Ser Phe Val Ser
            1               5                   10 aag acg gtt ttc gaa acg ctg cag aga ctg agg ggc gga gtc gtg ttg      277
Lys Thr Val Phe Glu Thr Leu Gln Arg Leu Arg Gly Gly Val Val Leu
            15                  20                  25 acg gaa tct gcg atc acc aaa ggt ttg cca tgc gtc gat agc ccg acg      325
Thr Glu Ser Ala Ile Thr Lys Gly Leu Pro Cys Val Asp Ser Pro Thr
        30                  35                  40 ccg atc gtt ctt ggg ttg tcg tcc tac ttg aca ttc gtg ttt ctc ggg      373
Pro Ile Val Leu Gly Leu Ser Ser Tyr Leu Thr Phe Val Phe Leu Gly
    45                  50                  55                  60 ctc att gtc atc aag agc ctg gat ctt aag ccc cgc tcc aag gag ccc      421
Leu Ile Val Ile Lys Ser Leu Asp Leu Lys Pro Arg Ser Lys Glu Pro
                65                  70                  75 gcc att ttg aac ctg ttt gtg atc ttc cac aac ttc gtc tgc ttc gca      469
Ala Ile Leu Asn Leu Phe Val Ile Phe His Asn Phe Val Cys Phe Ala
            80                  85                  90 ctc agt ctg tac atg tgc gtg gga att gtc cgt caa gct atc ctc aac      517
Leu Ser Leu Tyr Met Cys Val Gly Ile Val Arg Gln Ala Ile Leu Asn
        95                 100                 105 agg tac tct ctg tgg ggc aat gcg tac aat ccc aaa gaa gtt caa atg      565
Arg Tyr Ser Leu Trp Gly Asn Ala Tyr Asn Pro Lys Glu Val Gln Met
    110                 115                 120 ggc cac ctg ctc tac att ttc tac atg tca aag tac atc gag ttt atg      613
Gly His Leu Leu Tyr Ile Phe Tyr Met Ser Lys Tyr Ile Glu Phe Met
125                 130                 135                 140 gac acg gtc att atg att ttg aag cgc aac acg cgc cag atc act gtg      661
Asp Thr Val Ile Met Ile Leu Lys Arg Asn Thr Arg Gln Ile Thr Val
```

|   |   |   |   |   |   |   |   |   |   |   |   |   |   |   |   |     |
|---|---|---|---|---|---|---|---|---|---|---|---|---|---|---|---|-----|
|   |   |   |   | 145 |   |   |   |   | 150 |   |   |   |   | 155 |   |     |
| ttg | cat | gtg | tac | cac | cac | gca | tcc | atc | tcc | ttc | atc | tgg | tgg | atc | atc | 709 |
| Leu | His | Val | Tyr | His | His | Ala | Ser | Ile | Ser | Phe | Ile | Trp | Trp | Ile | Ile |     |
|   |   |   | 160 |   |   |   |   | 165 |   |   |   |   | 170 |   |   |     |
| gcc | tac | cat | gct | cct | ggc | ggt | gaa | gct | tat | ttc | tct | gcc | gca | ttg | aac | 757 |
| Ala | Tyr | His | Ala | Pro | Gly | Gly | Glu | Ala | Tyr | Phe | Ser | Ala | Ala | Leu | Asn |     |
|   |   | 175 |   |   |   |   | 180 |   |   |   |   | 185 |   |   |   |     |
| tcc | gga | gta | cat | gtg | ctc | atg | tac | ctc | tac | tac | ctt | ttg | gca | gca | act | 805 |
| Ser | Gly | Val | His | Val | Leu | Met | Tyr | Leu | Tyr | Tyr | Leu | Leu | Ala | Ala | Thr |     |
|   | 190 |   |   |   |   | 195 |   |   |   |   | 200 |   |   |   |   |     |
| ctg | gga | aag | aac | gag | aaa | gct | cgc | cgc | aag | tac | cta | tgg | tgg | gga | aaa | 853 |
| Leu | Gly | Lys | Asn | Glu | Lys | Ala | Arg | Arg | Lys | Tyr | Leu | Trp | Trp | Gly | Lys |     |
| 205 |   |   |   |   | 210 |   |   |   |   | 215 |   |   |   |   | 220 |     |
| tac | ttg | aca | cag | ctg | cag | atg | ttc | cag | ttt | gtc | ctt | aac | atg | att | cag | 901 |
| Tyr | Leu | Thr | Gln | Leu | Gln | Met | Phe | Gln | Phe | Val | Leu | Asn | Met | Ile | Gln |     |
|   |   |   | 225 |   |   |   |   | 230 |   |   |   |   | 235 |   |   |     |
| gct | tac | tac | gat | att | aag | aac | aac | tcg | cct | tac | cca | caa | ttt | ttg | atc | 949 |
| Ala | Tyr | Tyr | Asp | Ile | Lys | Asn | Asn | Ser | Pro | Tyr | Pro | Gln | Phe | Leu | Ile |     |
|   |   | 240 |   |   |   |   | 245 |   |   |   |   | 250 |   |   |   |     |
| cag | att | ttg | ttc | tac | tac | atg | atc | tcg | ctt | tta | gcg | cta | ttt | gga | aac | 997 |
| Gln | Ile | Leu | Phe | Tyr | Tyr | Met | Ile | Ser | Leu | Leu | Ala | Leu | Phe | Gly | Asn |     |
|   | 255 |   |   |   |   | 260 |   |   |   |   | 265 |   |   |   |   |     |
| ttt | tac | gtt | cac | aaa | tac | gta | tca | gcg | ccc | gca | aaa | cct | gcg | aag | atc | 1045 |
| Phe | Tyr | Val | His | Lys | Tyr | Val | Ser | Ala | Pro | Ala | Lys | Pro | Ala | Lys | Ile |     |
| 270 |   |   |   |   | 275 |   |   |   |   | 280 |   |   |   |   |   |     |
| aag | agc | aaa | aag | gca | gaa | taa | gacaccaccc | tagtgacaag | aagattttac |   |   |   |   |   |   | 1096 |
| Lys | Ser | Lys | Lys | Ala | Glu |   |   |   |   |   |   |   |   |   |   |     |
| 285 |   |   |   |   | 290 |   |   |   |   |   |   |   |   |   |   |     |

| | |
|---|---|
| actaaactgt agttttagca cccatcgttg acacgaatac attctggttc tgcctgtctt | 1156 |
| ggaagagtcg aagcattcag gagctctccc gttccatcga tcaaactcgg aacgaagtgc | 1216 |
| accttttagc tgcgatgaga gtctttactt cctgagccgt cgttcttgat gtggtctgta | 1276 |
| gctcagccat acgtgtagca tagctggaac atctggcttt tcaggaaagt cggcaaggca | 1336 |
| agaattcgac ccttgaacta dacaaggttc tgctgattca gcaaccatta gtgagtcact | 1396 |
| ggttaacaaa atcacagttt tgggccctta gttagtgaca accaaccctα acactttgat | 1456 |
| acacgagtta tcgttcgcga gtggaagtgt aaaaatgtgc tttcccaatc atcttgagtt | 1516 |
| ggttcctttt gaagtaaagg aaaattctat gattgttgag tccaaaaaaa aaaaaaaaaa | 1576 |
| a | 1577 |

<210> SEQ ID NO 4
<211> LENGTH: 290
<212> TYPE: PRT
<213> ORGANISM: Marchantia polymorpha

<400> SEQUENCE: 4

Met Glu Ala Tyr Glu Met Val Asp Ser Phe Val Ser Lys Thr Val Phe
 1               5                  10                  15

Glu Thr Leu Gln Arg Leu Arg Gly Gly Val Val Leu Thr Glu Ser Ala
            20                  25                  30

Ile Thr Lys Gly Leu Pro Cys Val Asp Ser Pro Thr Pro Ile Val Leu
        35                  40                  45

Gly Leu Ser Ser Tyr Leu Thr Phe Val Phe Leu Gly Leu Ile Val Ile
    50                  55                  60

Lys Ser Leu Asp Leu Lys Pro Arg Ser Lys Glu Pro Ala Ile Leu Asn
65                  70                  75                  80

Leu Phe Val Ile Phe His Asn Phe Val Cys Phe Ala Leu Ser Leu Tyr

```
                   85                  90                  95
Met Cys Val Gly Ile Val Arg Gln Ala Ile Leu Asn Arg Tyr Ser Leu
            100                 105                 110

Trp Gly Asn Ala Tyr Asn Pro Lys Glu Val Gln Met Gly His Leu Leu
            115                 120                 125

Tyr Ile Phe Tyr Met Ser Lys Tyr Ile Glu Phe Met Asp Thr Val Ile
        130                 135                 140

Met Ile Leu Lys Arg Asn Thr Arg Gln Ile Thr Val Leu His Val Tyr
145                 150                 155                 160

His His Ala Ser Ile Ser Phe Ile Trp Trp Ile Ile Ala Tyr His Ala
                165                 170                 175

Pro Gly Gly Glu Ala Tyr Phe Ser Ala Ala Leu Asn Ser Gly Val His
            180                 185                 190

Val Leu Met Tyr Leu Tyr Tyr Leu Leu Ala Ala Thr Leu Gly Lys Asn
        195                 200                 205

Glu Lys Ala Arg Arg Lys Tyr Leu Trp Trp Gly Lys Tyr Leu Thr Gln
210                 215                 220

Leu Gln Met Phe Gln Phe Val Leu Asn Met Ile Gln Ala Tyr Tyr Asp
225                 230                 235                 240

Ile Lys Asn Asn Ser Pro Tyr Pro Gln Phe Leu Ile Gln Ile Leu Phe
                245                 250                 255

Tyr Tyr Met Ile Ser Leu Leu Ala Leu Phe Gly Asn Phe Tyr Val His
            260                 265                 270

Lys Tyr Val Ser Ala Pro Ala Lys Pro Ala Lys Ile Lys Ser Lys Lys
        275                 280                 285

Ala Glu
    290

<210> SEQ ID NO 5
<211> LENGTH: 2307
<212> TYPE: DNA
<213> ORGANISM: Marchantia polymorpha
<220> FEATURE:
<221> NAME/KEY: CDS
<222> LOCATION: (375)..(1829)

<400> SEQUENCE: 5
tcacattgct ggtcgtcgga gggaggtgca caatctgggg ggctgtcatc aatgcgacgg      60
tgtttcgaag agatcgctgc gagtggcgct gagtttcttg ccgctttcta cctgagctga     120
tgcctgctgc tgctgcctag agctgcttgg tgctgcttgg ggctgctata agagcgcgtc     180
gacagcgagt gtctctcgcg gtcctcattc gtggggtgct gtcgttccag tttagagccc     240
gctggacgta cagccggtgc tggaaattga ttttgtgaaa agcgagccta cctctatcca     300
tcatcgtcgc ccgtggtggc agatcttccg gattcctcat gcgcggatcg tggtcgcttt     360
gaaggtcgac agtt atg ccg cca cac gcc cct gac tcc aca ggt ctt ggg      410
             Met Pro Pro His Ala Pro Asp Ser Thr Gly Leu Gly
               1               5                  10 ccc gaa gtt ttc cgc ctg cct gat gac gcg atc ccg gcc cag gat cgc      458
Pro Glu Val Phe Arg Leu Pro Asp Asp Ala Ile Pro Ala Gln Asp Arg
         15                  20                  25 aga tct aca cag aag aaa tac tcg ctt tca gac gtc agc aag cac aac      506
Arg Ser Thr Gln Lys Lys Tyr Ser Leu Ser Asp Val Ser Lys His Asn
     30                  35                  40 act ccg aat gat tgc tgg ctc gta att tgg ggg aag gtg tac gat gtt      554
Thr Pro Asn Asp Cys Trp Leu Val Ile Trp Gly Lys Val Tyr Asp Val
 45                  50                  55                  60
```

| | | |
|---|---|---|
| act tcg tgg gtt aag gtc cat cca ggt gga agt ctc atc ttt gtg aag<br>Thr Ser Trp Val Lys Val His Pro Gly Gly Ser Leu Ile Phe Val Lys<br>              65                          70                        75 | | 602 |
| gcg gga cag gat tca aca caa ctc ttt gat tct tat cac ccc ctc tat<br>Ala Gly Gln Asp Ser Thr Gln Leu Phe Asp Ser Tyr His Pro Leu Tyr<br>         80                          85                        90 | | 650 |
| gtc aga aag cta ctt gca cag ttc tgc att ggt gaa ctc caa acg agt<br>Val Arg Lys Leu Leu Ala Gln Phe Cys Ile Gly Glu Leu Gln Thr Ser<br>            95                        100                      105 | | 698 |
| gcg gga gat gag aag ttc aag tct tca acg ttg gag tat gct ggt gaa<br>Ala Gly Asp Glu Lys Phe Lys Ser Ser Thr Leu Glu Tyr Ala Gly Glu<br>        110                       115                      120 | | 746 |
| gaa cat gaa gta ttt tac cac act ctc aag cag cgc gtg gaa acg tac<br>Glu His Glu Val Phe Tyr His Thr Leu Lys Gln Arg Val Glu Thr Tyr<br>125                    130                      135                      140 | | 794 |
| ttc cgc aag cag aag ata aat cct cga tac cat ccg caa atg ctt gtg<br>Phe Arg Lys Gln Lys Ile Asn Pro Arg Tyr His Pro Gln Met Leu Val<br>                   145                      150                      155 | | 842 |
| aag tca gcc gtg atc att gga acc ctt ctt ctc tgt tac tat ttt ggc<br>Lys Ser Ala Val Ile Ile Gly Thr Leu Leu Leu Cys Tyr Tyr Phe Gly<br>        160                       165                      170 | | 890 |
| ttc ttc tgg tct caa aat gta ctc ctc tcg atg ttt ctg gca agc atc<br>Phe Phe Trp Ser Gln Asn Val Leu Leu Ser Met Phe Leu Ala Ser Ile<br>            175                      180                      185 | | 938 |
| atg ggg ttc tgc act gcg gag gtg ggc atg tcc atc atg cac gat ggt<br>Met Gly Phe Cys Thr Ala Glu Val Gly Met Ser Ile Met His Asp Gly<br>        190                       195                      200 | | 986 |
| aac cac gga tcg tac aca caa tct acc ttg ctt ggt tac gtc atg ggc<br>Asn His Gly Ser Tyr Thr Gln Ser Thr Leu Leu Gly Tyr Val Met Gly<br>205                      210                      215                      220 | | 1034 |
| gcc act ctt gat ctg gtg gga gct agc agt ttc atg tgg agg cag cag<br>Ala Thr Leu Asp Leu Val Gly Ala Ser Ser Phe Met Trp Arg Gln Gln<br>                       225                      230                      235 | | 1082 |
| cat gtg gcc ggg cac cac tcg ttc acc aac atc gac cat tac gat cca<br>His Val Ala Gly His His Ser Phe Thr Asn Ile Asp His Tyr Asp Pro<br>        240                       245                      250 | | 1130 |
| gac att cgt gtg aag gat cct gat tta cga cgg gtt act tct caa caa<br>Asp Ile Arg Val Lys Asp Pro Asp Leu Arg Arg Val Thr Ser Gln Gln<br>            255                      260                      265 | | 1178 |
| ccc cga aga tgg ttt cac gag tat cag cat atc tac tta gga gta ctc<br>Pro Arg Arg Trp Phe His Glu Tyr Gln His Ile Tyr Leu Gly Val Leu<br>        270                       275                      280 | | 1226 |
| tat ggc gtt ctt gcc tta aaa agt gtg ttg att gat gat ttc agc gcc<br>Tyr Gly Val Leu Ala Leu Lys Ser Val Leu Ile Asp Asp Phe Ser Ala<br>285                      290                      295                      300 | | 1274 |
| ttc ttc agt ggt gct atc ggc cca gta aag ata gct caa atg aca cca<br>Phe Phe Ser Gly Ala Ile Gly Pro Val Lys Ile Ala Gln Met Thr Pro<br>                   305                      310                      315 | | 1322 |
| ctc gag atg ggc gtc ttc tgg gga ggg aag gtt gtg tac gca ctg tac<br>Leu Glu Met Gly Val Phe Trp Gly Gly Lys Val Val Tyr Ala Leu Tyr<br>        320                       325                      330 | | 1370 |
| atg ttt ttg ctc cct atg atg tat ggt caa tac aac att ctt act ttc<br>Met Phe Leu Leu Pro Met Met Tyr Gly Gln Tyr Asn Ile Leu Thr Phe<br>            335                      340                      345 | | 1418 |
| att ggt ctc tac att ctc tca cag tta gtt gca ggg tgg act ctt gcc<br>Ile Gly Leu Tyr Ile Leu Ser Gln Leu Val Ala Gly Trp Thr Leu Ala<br>        350                       355                      360 | | 1466 |
| ctc ttc ttt caa gta gca cac gtt gtc gac gat gca gta ttt ccc gtt<br>Leu Phe Phe Gln Val Ala His Val Val Asp Asp Ala Val Phe Pro Val<br>365                      370                      375                      380 | | 1514 |

```
gcg gaa aca gat ggt gga aaa gca aag att cct tct ggt tgg gca gaa   1562
Ala Glu Thr Asp Gly Gly Lys Ala Lys Ile Pro Ser Gly Trp Ala Glu
            385                 390                 395 atg cag gtc aga acc act acc aat ttc agc tca cga tca atg ttc tgg   1610
Met Gln Val Arg Thr Thr Thr Asn Phe Ser Ser Arg Ser Met Phe Trp
        400                 405                 410 aca cat att agt ggc ggt ctg aac cat cag atc gag cac cat ctt ttc   1658
Thr His Ile Ser Gly Gly Leu Asn His Gln Ile Glu His His Leu Phe
    415                 420                 425 ccg ggt gtc tgt cat gtt cac tac cca agc ata cag cca atc gtg aag   1706
Pro Gly Val Cys His Val His Tyr Pro Ser Ile Gln Pro Ile Val Lys
430                 435                 440 gct acc tgt gac gag ttc aac gtg cct tat act tcc tac ccc act ttc   1754
Ala Thr Cys Asp Glu Phe Asn Val Pro Tyr Thr Ser Tyr Pro Thr Phe
445                 450                 455                 460 tgg gcg gcc ctt agg gca cat ttt caa cat ctg aaa aac gtc gga cta   1802
Trp Ala Ala Leu Arg Ala His Phe Gln His Leu Lys Asn Val Gly Leu
                465                 470                 475 caa gat gga cta cga ctg gat ggc tga actgtgacag catgctttgg         1849
Gln Asp Gly Leu Arg Leu Asp Gly
            480 gcctgcactt tcagatttcg gatcgaaggt gcgggcgatg gaaataatca gataagagtt 1909 gtaagtaacg ttcaggagga gagcagaacg gattgatgag tgtccatttg tgaggcttcc 1969 acctttcagg aacagaagtt gattcgaatg cgaaacctcc aatgagcatt tcacagccgt 2029 cttctccttg gccatcatgt gttcctccta gggagcttcg gttttggaa gttagtcagc  2089 ttactttcga agatcgttca acgctcaagg ctagattttg tcgacactat ttagttaggt 2149 ccgatagata ggtgataaga ttccggtgcc ctcacacatg tttcatcagt tgcgatgtaa 2209 ttccagtaat ccacgtatgt ggctccagtg tctgctgaaa tcagcacagg cagctatatc 2269 atgctccttg atctctaaaa aaaaaaaaaa aaaaaaaa                         2307

<210> SEQ ID NO 6
<211> LENGTH: 484
<212> TYPE: PRT
<213> ORGANISM: Marchantia polymorpha

<400> SEQUENCE: 6

Met Pro Pro His Ala Pro Asp Ser Thr Gly Leu Gly Pro Glu Val Phe
1               5                   10                  15

Arg Leu Pro Asp Asp Ala Ile Pro Ala Gln Asp Arg Arg Ser Thr Gln
            20                  25                  30

Lys Lys Tyr Ser Leu Ser Asp Val Ser Lys His Asn Thr Pro Asn Asp
        35                  40                  45

Cys Trp Leu Val Ile Trp Gly Lys Val Tyr Asp Val Thr Ser Trp Val
    50                  55                  60

Lys Val His Pro Gly Gly Ser Leu Ile Phe Val Lys Ala Gly Gln Asp
65                  70                  75                  80

Ser Thr Gln Leu Phe Asp Ser Tyr His Pro Leu Tyr Val Arg Lys Leu
                85                  90                  95

Leu Ala Gln Phe Cys Ile Gly Glu Leu Gln Thr Ser Ala Gly Asp Glu
            100                 105                 110

Lys Phe Lys Ser Ser Thr Leu Glu Tyr Ala Gly Glu Glu His Glu Val
        115                 120                 125

Phe Tyr His Thr Leu Lys Gln Arg Val Glu Thr Tyr Phe Arg Lys Gln
    130                 135                 140

Lys Ile Asn Pro Arg Tyr His Pro Gln Met Leu Val Lys Ser Ala Val
```

```
                145                 150                 155                 160
Ile Ile Gly Thr Leu Leu Leu Cys Tyr Tyr Phe Gly Phe Phe Trp Ser
                165                 170                 175

Gln Asn Val Leu Leu Ser Met Phe Leu Ala Ser Ile Met Gly Phe Cys
            180                 185                 190

Thr Ala Glu Val Gly Met Ser Ile Met His Asp Gly Asn His Gly Ser
        195                 200                 205

Tyr Thr Gln Ser Thr Leu Leu Gly Tyr Val Met Gly Ala Thr Leu Asp
    210                 215                 220

Leu Val Gly Ala Ser Ser Phe Met Trp Arg Gln Gln His Val Ala Gly
225                 230                 235                 240

His His Ser Phe Thr Asn Ile Asp His Tyr Asp Pro Asp Ile Arg Val
                245                 250                 255

Lys Asp Pro Asp Leu Arg Arg Val Thr Ser Gln Gln Pro Arg Arg Trp
            260                 265                 270

Phe His Glu Tyr Gln His Ile Tyr Leu Gly Val Leu Tyr Gly Val Leu
        275                 280                 285

Ala Leu Lys Ser Val Leu Ile Asp Asp Phe Ser Ala Phe Phe Ser Gly
    290                 295                 300

Ala Ile Gly Pro Val Lys Ile Ala Gln Met Thr Pro Leu Glu Met Gly
305                 310                 315                 320

Val Phe Trp Gly Gly Lys Val Val Tyr Ala Leu Tyr Met Phe Leu Leu
                325                 330                 335

Pro Met Met Tyr Gly Gln Tyr Asn Ile Leu Thr Phe Ile Gly Leu Tyr
            340                 345                 350

Ile Leu Ser Gln Leu Val Ala Gly Trp Thr Leu Ala Leu Phe Phe Gln
    355                 360                 365

Val Ala His Val Val Asp Asp Ala Val Phe Pro Val Ala Glu Thr Asp
370                 375                 380

Gly Gly Lys Ala Lys Ile Pro Ser Gly Trp Ala Glu Met Gln Val Arg
385                 390                 395                 400

Thr Thr Thr Asn Phe Ser Ser Arg Ser Met Phe Trp Thr His Ile Ser
                405                 410                 415

Gly Gly Leu Asn His Gln Ile Glu His His Leu Phe Pro Gly Val Cys
            420                 425                 430

His Val His Tyr Pro Ser Ile Gln Pro Ile Val Lys Ala Thr Cys Asp
    435                 440                 445

Glu Phe Asn Val Pro Tyr Thr Ser Tyr Pro Thr Phe Trp Ala Ala Leu
    450                 455                 460

Arg Ala His Phe Gln His Leu Lys Asn Val Gly Leu Gln Asp Gly Leu
465                 470                 475                 480

Arg Leu Asp Gly

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)
<223> OTHER INFORMATION: a, c, g, t, unknown or other

<400> SEQUENCE: 7
tggtggaarg anaarcayaa                                              20
```

```
<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)
<223> OTHER INFORMATION: inosine
<220> FEATURE:
<221> NAME/KEY: modified_base
<222> LOCATION: (7)
<223> OTHER INFORMATION: inosine
<220> FEATURE:
<221> NAME/KEY: modified_base
<222> LOCATION: (10)
<223> OTHER INFORMATION: inosine
<220> FEATURE:
<221> NAME/KEY: modified_base
<222> LOCATION: (13)
<223> OTHER INFORMATION: inosine

<400> SEQUENCE: 8
rttnarnccn ccngtraacc a                                              21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagttgcctt cgatgtttct gg                                             22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctcgcctgg agcaaggaaa tc                                             22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (18)
<223> OTHER INFORMATION: inosine

<400> SEQUENCE: 11
gtngarttya tggayacngt                                                20

<210> SEQ ID NO 12
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (12)
<223> OTHER INFORMATION: inosine

<400> SEQUENCE: 12
cknccccara anarrtaytt                                                    20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcgagctttc tcgttctttc cc                                                 22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tatgattttg aagcgcaaca cg                                                 22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (14)
<223> OTHER INFORMATION: inosine

<400> SEQUENCE: 15
athrangrna artntaygay gt                                                 22

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
```

```
<223> OTHER INFORMATION: inosine
<220> FEATURE:
<221> NAME/KEY: modified_base
<222> LOCATION: (6)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (18)
<223> OTHER INFORMATION: inosine

<400> SEQUENCE: 16
ggnaynkwnt sdatrtcngg rtc                                           23

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtgtgtacga tccgtggtta cc                                            22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaggcgggac aggattcaac ac                                            22

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggaattcgcg atggcctcgt ccaccaccac                                    30

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggaattctac tttcgcagcg tatgctacc                                     29

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
```

```
ggaattcgcg atggaggcgt acgagatgg                                              29
```

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
ggaattcttc tgccttttg ctcttgatc                                               29
```

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
gttgaattcg acagttatgc cgccacacgc                                             30
```

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
gttgaattca ggcccaaagc atgctgtcac                                             30
```

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
cgggatcctc tcctggcgca ccatcgtc                                               28
```

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
ggggtaccaa cgcgctttcc caccaacg                                               28
```

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
gctctagagc gatggcctcg tccaccacc                                              29
```

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gctctagact atactttcgc agcgtatgc                                    29

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctctagagc gatggaggcg tacgagatgg                                   30

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gctctagatt attctgcctt tttgctc                                      27

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gctctagaga cagttatgcc gccacacgc                                    29

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gctctagaag gcccaaagca tgctgtcac                                    29

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caggaaacag ctatgacc                                                18

```
<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaactgcaga ttcccgatct agtaacatag                                       30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccggaattcg catgcctgca ggtccccaga                                       30

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgtaaaacga cggccagt                                                    18

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Glu or Asp

<400> SEQUENCE: 37

Trp Trp Lys Xaa Lys His Asn
  1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Phe Thr Gly Gly Leu Asn
  1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39
```

Val Glu Phe Met Asp Thr Val
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Tyr Leu Phe Trp Gly Arg
 1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Glu or Asn
<220> FEATURE:
<221> NAME/KEY: MOD_RES
<222> LOCATION: (3)
<223> OTHER INFORMATION: Gly or Asp

<400> SEQUENCE: 41

Ile Xaa Xaa Lys Val Tyr Asp Val
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Gln or Asp
<220> FEATURE:
<221> NAME/KEY: MOD_RES
<222> LOCATION: (6)
<223> OTHER INFORMATION: Tyr or Thr
<220> FEATURE:
<221> NAME/KEY: MOD_RES
<222> LOCATION: (7)
<223> OTHER INFORMATION: Met or Val

<400> SEQUENCE: 42

Asp Pro Asp Ile Xaa Xaa Xaa Pro
 1               5

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agtctctaga gcgatggagg cgtacg                                          26

```
<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cagtgagctc ggtgtcttat tctgcc                                          26

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agcttctaga gccatgccgc cacacgccc                                       29

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cagtgagctc tcagccatcc agtcgt                                          26
```

MARCHANTIALES-DERIVED UNSATURATED FATTY ACID SYNTHETASE GENES AND USE OF THE SAME

CROSS REFERENCE TO RELATED APPLICATIONS

This application is a division of application Ser. No. 10/584,082, filed May 15, 2007, now U.S. Pat. No. 7,915,487 B2, which is a National Stage of International Application No. PCT/JP2004/019196, filed Dec. 22, 2004, which claims the benefit of Japanese Patent Application No. 2003-425673, filed on Dec. 22, 2003, and which are incorporated by reference herein in their entirety.

TECHNICAL FIELD

The present invention relates to Marchantiales (*Marchantia polymorpha*)-derived unsaturated fatty acid synthetase genes, i.e. genes of Δ5 fatty acid desaturase, Δ6 fatty acid desaturase, and Δ6 fatty-acid-chain elongase, and use thereof.

BACKGROUND ART

Polyunsaturated fatty acids (PUFAs) such as arachidonic acid, eicosapentaenoic acid (hereinafter referred to as "EPA" as appropriate) are contained in lipids of the cell membrane of humans, notably in the nervous system. These polyunsaturated fatty acids act as a precursor of a bioactive substance such as prostaglandin and leukotriene, and are very important pharmacological substances. In recent years, health foods containing arachidonic acid and EPA have been commercially available. In addition, fatty acids, which are used as a source material of detergents and biodegradable plastics, have captured the spotlight as material substances.

Polyunsaturated fatty acids are currently produced by extraction from cultured microorganisms or fish oil. This raises problems of high production cost, increased energy consumption and waste, and limited fish resources particularly in methods using fish oil.

The biosynthesis of arachidonic acid and EPA is believed to occur in a series of reactions involving Δ6 desaturation, chain elongation, and Δ5 desaturation, with linoleic acid and α-linolenic acid being starting materials of the reactions yielding the arachidonic acid and eicosapentaenoic acid, respectively. These reactions are catalyzed by a Δ6 fatty acid desaturase ("Δ6 desaturase" hereinafter), Δ6 fatty-acid-chain elongase ("Δ6 chain elongase" hereinafter), and Δ5 fatty acid desaturase ("Δ5 desaturase" hereinafter), respectively.

A gene for the Δ6 desaturase is cloned from several plant species. For example, the gene has been cloned from *Phaeodactylum tricornutum*, *Physcomitrella patens*, ceratodon purpureous, borage, lithospermum erythrorhizon, primrose, and anemone. Apart from plants, the Δ6 desaturase gene has also been cloned from filamentous fungi, nematodes, cyanobacteria, rats, and humans (see Non-Patent Publication 1: Eur. J. Biochem. 269, p4105, 2002; Non-Patent Publication 2: Plant J. 15, p39, 1998; Non-Patent Publication 3: Eur. J. Biochem., 267. p3801, 2000; Non-Patent Publication 4: Proc. Natl. Acad. Sci. USA 94, p4211, 1997; Non-Patent Publication 5: Lipids 37, 417, 2002; Non-Patent Publication 6: FEBS Lett. 542, p100, 2003; Non-Patent Publication 7: Whitney et al., Planta Epub 2003; Non-Patent Publication 8: Lipids 34, p649, 1999; Non-Patent Publication 9: Gene, 238, p445 1999; Non-Patent Publication 10: Biochem J. 330, p611 1998; Non-Patent Publication 11: Plant Mol. Biol., 22, p293 1993; Non-Patent Publication 12: Biochem. Biophys. res. Commun. 255, p575, 1999; and Non-Patent Publication 13: J. Biol. Chem. 274, p471, 1999). All of these Δ6 desaturates cloned from these organisms, except that obtained from cyanobacteria, have a cytochrome b5 domain at their N-terminus.

A gene of the Δ6 chain elongase was originally cloned from filamentous fungi and nematodes (see Non-Patent Publication 14: Proc. Natl. Acad. Sci. USA 97, p8284, 2000; and Non-Patent Publication 15: Proc. Natl. Acad. Sci. USA 97, p64-21, 2000). In plants, the gene has been cloned only from *Physcomitrella patens* (see Non-Patent Publication 16: Plant J. 31, p255, 2002).

In yeasts (*Saccharomyces cerevisiae*), there exist ELO2 protein and ELO3 protein, which are involved in the synthesis of a long-chain saturated acyl-chain of sphingolipids (see Non-Patent Publication 17: J. Biol. Chem., 272, p17376, 1997). The Δ6 chain elongase has an amino acid sequence homologous to the ELO2 protein and ELO3 protein. On the other hand, in plants, there exists β-ketoacyl-CoA synthase (KCS), which is another type of fatty-acid-chain elongase. This enzyme catalyzes the elongation of long-chain saturated and monounsaturated fatty acids (see Non-Patent Publication 15 and Non-Patent Publication 18: Plant Cell 7, p309, 1995). However, the KCS gene is not evolutionary related to the Δ6 chain elongase gene, or yeast ELO2 and ELO3 genes (see Non-Patent Publications 15 and 16).

A gene of the Δ5 desaturase was originally cloned from filamentous fungi (Non-Patent Publication 19: J. Biol. Chem. 273, p29360, 1998; and Non-Patent Publication 20: J. Biol. Chem. 273, p19055). The Δ5 desaturase has a cytochrome b5 domain at the N-terminus as does the Δ6 desaturase. The Δ5 desaturase gene has also been cloned from Phaeodactylum tricornutum, nematodes, rats, humans, *Physcomitrella patens*, and others (see Non-Patent Publication 1; Non-Patent Publication 21: FEBS Lett. 439, p215, 1998; Non-Patent Publication 22: Arch. Biochem. Biophys. 391, p8, 2001; Non-Patent Publication 23: J. Biol. Chem. 274, p37335, 1999; and Non-Patent Publication 24: J. Biol. Chem. 278, 35115, 2003).

Terrestrial plants are classified into bryophytes (Bryophyta), pteridophytes, gymnosperms, and angiosperms. Among these groups of terrestrial plants, bryophytes are known to have branched off first, and they are classified into three groups: Mosses (class Bryosida), Liverworts (class Hepaticopsida), and Hornwortz. *Marchantia polymorpha* is taxonomicafly closest to Physcomitrella patens among the foregoing organisms, but the latter belongs to class Bryosida while the former belongs to subclass Marchanttiidae of class Hepaticopsida. It is certain that the foregoing three groups were branched off at least about 430 million years ago. Therefore, contrary to their common name "moss," the difference between Physcomitrella patens and *Marchantia polymorpha* is evolutionary far too great to be called as a difference, as compared with the difference, for example, between *Arabidopsis thaliana* and rice, which are believed to have branched off 200 million years ago (see Non-Patent Publication 25: www.nibb.ac.jp/~mhasebe/Physcomitrella.html).

As a *Marchantia polymorpha*-derived polyunsaturated fatty acid synthetase gene, KCS-like MpFAE2 and MpFAE3 chain elongase genes have been obtained (see Non-Patent Publication 26: Biosci. Biotechnol. Biochem. 67, p605, 2003; and Non-Patent Publication 27: Biosci. Biotechnol. Biochem. 67, p1667, 2003). However, MpFAE2 and MpFAE3 are not Δ6 chain elongase genes.

As described earlier, many polyunsaturated fatty acid biosynthetic genes are cloned from various species of organisms. However, there is only a few reports in which polyunsaturated fatty acids having 20 or more carbon atoms with a degree of unsaturation 4 or greater, such as arachidonic acid and EPA, were produced in plants. As an example, it has been reported that Phaeodactyllun tricornutum-derived Δ6 desaturase gene and Δ5 desaturase gene, and a Physcomitreila patens-derived Δ6 chain elongase gene were expressed in *Linum usitatissimum* to produce arachidonic acid and EPA. However, this is not described in detail (see Non-Patent Publication 24).

As described earlier, polyunsaturated fatty acids, such as arachidonic acid and EPA, are produced by extraction from cultured microorganisms or fish oil. This raises problems of high production cost, increased energy consumption and waste, and limited fish resources. Polyunsaturated fatty acids such as arachidonic acid and EPA have a plurality of double bonds in the molecule. This unique characteristic enables these fatty acids to be used in various industrial products (e.g. films, biodegradable plastics, functional fabrics, lubricating oil, and material substance for detergents). By producing such polyunsaturated fatty acids in transgenic plants, it will be possible to reduce production cost and realize a more environmentally friendly production process. Once the polyunsaturated fatty acids are mass-produced with oil plants by genetic recombinant techniques, it will be possible to advantageously use such oil plants as inexpensive source materials for many different purposes.

However, in the expression of foreign genes in plants, it is difficult to predict how well the genes will function in the plants because the gene expression involves transcription, translation, and modifications. Further, in the expression of more than one foreign gene, it is envisaged that the expressed genes will function more desirably when they come from a single species of plant, as opposed to different plant species as in the case of Non-Patent Publication 24. Further, *Marchantia polymorpha*, which belongs to phylum Bryophyta—the first terrestrial plants—has been receiving attention as a model of higher plants, and their genes are expected to function well in other plants. Therefore, once *Marchantia polymorpha*-derived polyunsaturated fatty acid synthetase genes, i.e. Δ5 desaturase gene, Δ6 desaturase gene, and Δ6 chain elongase gene are obtained, it will be possible to efficiently accumulate arachidonic acid and EPA in plants by introducing these genes into plants.

The Δ5 desaturase gene, Δ6 desaturase gene, and Δ6 chain elongase gene have been cloned from *Physcomitrella patens*, which also belong to phylum bryophyta as does *Marchantia polymorpha*. However, since *Marchantia polymorpha* and *Physcomitrella patens* are evolutionary very distant species, it is not easy to obtain *Marchantia polymorpha* genes using *Physcomitrella patens* genes with the current level of technology.

DISCLOSURE OF INVENTION

The present invention was made in view of the foregoing problems, and an object of the invention is to provide Marchantiales (*Marchantia polymorpha*)-derived unsaturated fatty acid synthetase genes, specifically, Δ5 desaturase gene, Δ6 desaturase gene, and Δ6 chain elongase gene, that can produce arachidonic acid or EPA in higher plants. The invention also provides a method of use of such genes.

In accomplishing the present invention, the inventors of the invention identified genes that encode the Δ5 desaturase, Δ6 desaturase, and Δ6 chain elongase, using cDNA clones derived from Marchantiales (*Marchantia polymorpha*), and successfully transferred and expressed these genes in methylotrophic yeasts (*Pichia pastoris*). As a result, the inventors have found that proteins expressed by these genes had enzyme activities of the Δ5 desaturase, Δ6 desaturase, and Δ6 chain elongase, respectively. Specifically, the present invention includes:

(1) A Marchantiales-derived gene that hybridizes under stringent conditions with all of or part of a DNA nucleotide sequence, or its complementary sequence, of SEQ ID NO: 1, and encodes a protein having a Δ6 fatty acid desaturating activity.

(2) A gene that encodes a Marchantiales-derived protein having a Δ6 fatty acid desaturating activity, and that (a) consists of a nucleotide sequence of SEQ ID NO: 1, or (b) hybridizes under stringent conditions with a DNA nucleotide sequence, or its complementary sequence, of SEQ ID NO: 1.

(3) A gene that encodes a Marchantiales-derived protein having a Δ6 fatty acid desaturating activity, and that (a) consists of a nucleotide sequence of from the 253rd to 1698th nucleotides of SEQ ID NO: 1, or (b) hybridizes under stringent conditions with a DNA nucleotide sequence of from the 253rd to 1698th nucleotides, or its complementary sequence, of SEQ ID NO: 1.

(4) A gene that encodes a Marchantiales-derived protein having a Δ6 fatty acid desaturating activity, and that (a) encodes a protein with an amino acid sequence of SEQ ID NO: 2, or (b) encodes a protein with an amino acid sequence that has been modified by substitution, deletion, insertion, and/or addition of one or more amino acids of SEQ ID NO: 2.

(5) A Marchantiales-derived gene that hybridizes under stringent conditions with all of or part of a DNA nucleotide sequence, or its complementary sequence, of SEQ ID NO: 3, and encodes a protein having a Δ6 chain elongating activity.

(6) A gene that encodes a Marchantiales-derived protein having a Δ6 chain elongating activity, and that (a) consists of a nucleotide sequence of SEQ ID NO: 3, or (b) hybridizes under stringent conditions with a DNA nucleotide sequence, or its complementary sequence, of SEQ ID NO: 3.

(7) A gene that encodes a Marchantiales-derived protein having a Δ6 chain elongating activity, and that (a) consists of a nucleotide sequence of from the 194th to 1066th nucleotides of SEQ ID NO: 3, or (b) hybridizes under stringent conditions with a DNA nucleotide sequence of from the 194th to 1066th nucleotides, or its complementary sequence, of SEQ ID NO: 3.

(8) A gene that encodes a Marchantiales-derived protein having a Δ6 chain elongating activity, and that (a) encodes a protein with an amino acid sequence of SEQ ID NO: 4, or (b) encodes a protein with an amino acid sequence that has been modified by substitution, deletion, insertion, and/or addition of one or more amino acids of SEQ ID NO: 4.

(9) A Marchantiales-derived gene that hybridizes under stringent conditions with all of or part of a DNA nucleotide sequence, or its complementary sequence, of SEQ ID NO: 5, and encodes a protein having a Δ5 fatty acid desaturating activity.

(10) A gene that encodes a Marchantiales-derived protein having a Δ5 fatty acid desaturating activity, and that (a) consists of a nucleotide sequence of SEQ ID NO: 5, or (b) hybridizes under stringent conditions with a DNA nucleotide sequence, or its complementary sequence, of SEQ ID NO: 5.

(11) A gene that encodes a Marchantiales-derived protein having a Δ5 fatty acid desaturating activity, and that (a) consists of a nucleotide sequence of from the 375th to 1829th nucleotides of SEQ ID NO: 5, or (b) hybridizes under stringent conditions with a DNA nucleotide sequence of from 375th to 1829th nucleotides, or its complementary sequence, of SEQ ID NO: 5.

(12) A gene that encodes a Marchantiales-derived protein having a Δ5 fatty acid desaturating activity, and that (a)

encodes a protein with an amino acid sequence of SEQ ID NO: 6, or (b) encodes a protein with an amino acid sequence that has been modified by substitution, deletion, insertion, and/or addition of one or more amino acids of SEQ ID NO: 6.

(13) A protein encoded by a gene of any one of genes (1) through (12).

(14) A protein (a) consisting of an amino acid sequence of SEQ ID NO: 2, or (b) consisting of an amino acid sequence that has been modified by substitution, deletion, insertion, and/or addition of one or more amino acids of SEQ ID NO: 2, and having a Δ6 fatty acid desaturating activity.

(15) A protein (a) consisting of an amino acid sequence of SEQ ID NO: 4, or (b) consisting of an amino acid sequence that has been modified by substitution, deletion, insertion, and/or addition of one or more amino acids of SEQ ID NO: 4, and having a Δ6 chain elongating activity.

(16) A protein (a) consisting of an amino acid sequence of SEQ ID NO: 6, or (b) consisting of an amino acid sequence that has been modified by substitution, deletion, insertion, and/or addition of one or more amino acids of SEQ ID NO: 6, and having a Δ5 fatty acid desaturating activity.

(17) An antibody which recognizes a protein of any one of proteins (13) through (16).

(18) A recombinant expression vector which comprises a gene of any one of genes (1) through (12).

(19) A transformant into which a gene of any one of genes (1) through (12) is introduced.

(20) A plant into which at least a gene of any one of genes (1) through (12) is expressibly introduced, its progeny or vegetatively propagated plants having the same characteristics, or a tissue of the plant.

(21) A plant into which at least a gene of any one of genes (1) through (12) is expressibly introduced and whose fatty acid composition is thereby modified, its progeny or vegetatively propagated plants having the same characteristics, or a tissue of the plant.

(22) A reproductive material of a plant (20) or (21).

(23) A method of producing fatty acids, using a plant or a plant tissue of (21).

(24) A material substance which includes at least one compound selected from the group consisting of: γ-linolenic acid; dihomo-γ-linolenic acid; arachidonic acid; stearidonic acid; eicosatetraenoic acid; and eicosapentaenoic acids, which are obtained by a method of (23).

(25) A method of modifying a fatty acid composition, using at least a gene of any one of (1) through (12).

(26) A gene detecting instrument comprising as a probe at least a portion of a nucleotide sequence, or its complementary sequence, of a gene of any one of (1) through (12).

(27) A screening method of a gene or substance that regulates a protein of any one of (13) through (16), using a protein of any one of (13) through (16).

(28) A gene or substance obtained by a screening method of (27).

It is to be noted that, in the present invention, the nucleotides A, C, G, and T indicate adenine, cytosine, guanine, and thymine, respectively, unless otherwise specified.

Other objects, features, and advantages of the invention will be made clear by the descriptions below. Benefits of the invention will also be made clear by the description referring to the attached drawing.

BRIEF DESCRIPTION OF DRAWINGS

FIG. 1 is an explanatory drawing illustrating a procedure of constructing a construct in which expression cassettes of MpDES6 gene, MpELO1 gene, and MpDES5 gene used in Example 6 are joined to one another.

BEST MODE FOR CARRYING OUT THE INVENTION

The following will describe an embodiment of the present invention. It is to be noted that the invention is not limited in any way by the following description. Specifically, the following describes, in order of appearance, synthetic pathways of arachidonic acid and eicosapentaenoic acid (EPA), genes and proteins according to the invention, methods of obtaining proteins and genes of the invention, and methods of use (usefulness) of genes and proteins according to the invention.

(1) Synthetic Pathways of Arachidonic Acid and Eicosapentaenoic Acid (EPA)

The biosynthesis of arachidonic acid and eicosapentaenoic acid (EPA) is believed to occur in a series of reactions involving Δ6 desaturation, Δ6 chain elongation, and Δ5 desaturation, with linoleic acid and α-linolenic acid being starting materials of the reactions yielding the arachidonic acid and eicosapentaenoic acid, respectively. These reactions are catalyzed by Δ6 desaturase, Δ6 chain elongase, and Δ5 desaturase, and are called an n-6 pathway (arachidonic acid synthetic pathway), or an n-3 pathway (EPA synthetic pathway).

Previous reports suggest that the Δ6 desaturase, Δ6 chain elongase, and Δ5 desaturase are involved in both n-6 pathway and n-3 pathway. Specifically, the Δ6 desaturase in the n-6 pathway converts linoleic acid ($18:2\Delta^{9,12}$, containing 18 carbon atoms, and two double bonds at positions 9 and 12 (the same notation will be used below)) into γ-linolenic acid (GLA; $18:3\Delta^{6,9,12}$). In the n-3 pathway, the Δ6 desaturase converts α-linolenic acid (ALA; $18:3\Delta^{9,12,15}$) into stearidonic acid (STA; $18:4\Delta^{6,9,12,15}$). The Δ6 chain elongase in the n-6 pathway converts GLA into dihomo-γ-linolenic acid (DGLA; $20:3\Delta^{8,11,14}$), and in the n-3 pathway converts STA into eicosatetraenoic acid (ETA; $20:4\Delta^{8,11,14,17}$). The Δ5 desaturase in the n-6 pathway converts DGLA into arachidonic acid ($20:4\Delta^{5,8,11,14}$), and in the n-3 pathway converts ETA into eicosapentaenoic acid (EPA; $20:5\Delta^{5,8,11,14,17}$).

(2) Genes According to the Present Invention

[Δ6 Desaturase Gene According to the Invention]

A Δ6 desaturase gene according to the present invention is a Marchantiales-derived gene that encodes a protein having a Δ6 fatty acid desaturating activity. Specifically, the gene satisfies the following conditions:

1. A gene with the nucleotide sequence of SEQ ID NO: 1;
2. A gene that hybridizes under stringent conditions with DNA of a nucleotide sequence, or its complementary sequence, of SEQ ID NO: 1;
3. A gene that hybridizes under stringent conditions with part of DNA of a nucleotide sequence, or its complementary sequence, of SEQ ID NO: 1;
4. A gene with a nucleotide sequence of from the 253rd to 1698th nucleotides of a nucleotide sequence of SEQ ID NO: 1, wherein this portion of the nucleotide sequence is translated into a protein with an amino acid sequence of SEQ ID NO: 2;
5. A gene that hybridizes under stringent conditions with a nucleotide sequence of from the 253rd to 1698th nucleotides of a nucleotide sequence, or its complementary sequence, of SEQ ID NO: 1;
6. A gene that encodes a protein with an amino acid sequence of SEQ ID NO: 2; and
7. A gene that encodes a protein with an amino acid sequence that has been modified by substitution, deletion, insertion, and/or addition of one or more amino acids of the amino acid sequence of SEQ ID NO: 2.

[Δ6 Chain Elongase Gene According to the Present Invention]

A Δ6 chain elongase gene according to the present invention is a Marchantiales-derived gene that encodes a protein having a Δ6 fatty-acid-chain elongating activity. Specifically, the gene satisfies the following conditions:

1. A gene with a nucleotide sequence of SEQ ID NO: 3;
2. A gene that hybridizes under stringent conditions with DNA of the nucleotide sequence, or its complementary sequence, of SEQ ID NO: 3;
3. A gene that hybridizes under stringent conditions with part of DNA of a nucleotide sequence, or its complementary sequence, of SEQ ID NO: 3;
4. A gene with a nucleotide sequence of from the 194th to 1066th nucleotides of a nucleotide sequence of SEQ ID NO: 3, wherein this portion of the nucleotide sequence is translated into a protein with an amino acid sequence of SEQ ID NO: 4;
5. A gene that hybridizes under stringent conditions with a nucleotide sequence of from the 194th to 1066th nucleotides of a nucleotide sequence, or its complementary sequence, of SEQ ID NO: 3;
6. A gene that encodes a protein with an amino acid sequence of SEQ ID NO: 4; and
7. A gene that encodes a protein with an amino acid sequence that has been modified by substitution, deletion, insertion, and/or addition of one or more amino acids of the amino acid sequence of SEQ ID NO: 4.

[Δ5 Desaturase Gene According to the Invention]

A Δ5 desaturase gene according to the present invention is a Marchantiales-derived gene that encodes a protein having a Δ5 fatty acid desaturating activity. Specifically, the gene satisfies the following conditions:

1. A gene with a nucleotide sequence of SEQ ID NO: 5;
2. A gene that hybridizes under stringent conditions with DNA of a nucleotide sequence, or its complementary sequence, of SEQ ID NO: 5;
3. A gene that hybridizes under stringent conditions with part of DNA of a nucleotide sequence, or its complementary sequence, of SEQ ID NO: 5;
4. A gene with a nucleotide sequence of from the 375th to 1829th nucleotides of a nucleotide sequence of SEQ ID NO: 5, wherein this portion of the nucleotide sequence is translated into a protein with an amino acid sequence of SEQ ID NO: 6;
5. A gene that hybridizes under stringent conditions with a nucleotide sequence of from the 375th to 1829th nucleotides, or its complementary sequence, of SEQ ID NO: 5;
6. A gene that encodes a protein with an amino acid sequence of SEQ ID NO: 6; and
7. A gene that encodes a protein with an amino acid sequence that has been modified by substitution, deletion, insertion, and/or addition of one or more amino acids of the amino acid sequence of SEQ ID NO: 6.

As used herein, "under stringent conditions" means that hybridization takes place only when there is at least 90% identity, preferably at least 95% identity, and more preferably at least 97% identity.

Hybridization may be carried out by a conventional method, as described in J. Sambrook et al. Molecular Cloning, A Laboratory Manual, 2nd Ed., Cold Spring Harbor Laboratory (1989), for example. Generally, the level of stringency increases with increase in temperature and/or decrease in salt concentration (more difficult to hybridize), and more homologous genes are obtained. Hybridization conditions are not particularly limited, and hybridization can be suitably carried out under various conditions known in the art. For example, hybridization can be carried out under the following conditions: 42° C., 6×SSPC, 50% formamide, 1% SDS, 100 µg/ml salmon sperm DNA, 5×Denhardt's solution (1×SSPE; 0.18 M sodium chloride, 10 mM sodium phosphate, pH 7.7, 1 mM EDTA).

As the term is used herein, "Marchantiales" is not just limited to *Marchantia polymorpha*, but includes all organisms that belong to subclass Marchantiidae and order Marchantiales. Among such Marchantiales organisms, the following species are known to contain super long polyunsaturated fatty acids (Prog. Lipid Res. 32, p281, 1993): *Monoclea forsteri* (Monocleales), *Corsinia coriandrina* (Marchantiales), *Oximitra paleacea* (Marchantiales), *Ricciocarpos natans* (Marchantiales), *Ricca hueberneriana* (Marchantiales), *Ricca fluitans* (Marchantiales), *Ricca duplex* (Marchantiales), *Ricca canaliculata* (Marchantiales), *Ricca bifurca* (Marchantiales), *Ricca ciliifera* (Marchantiales), *Ricca glauca* (Marchantiales), *Ricca sorocarpa* (Marchantiales), *Ricca warnstorfii* (Marchantiales), *Ricca michelii* (Marchantiales), *Ricca papillosa* (Marchantiales), and *Ricca zachariae* (Marchantiales). With the current techniques, the Δ6 desaturase, Δ6 chain elongase, and Δ5 desaturase genes can readily be obtained from these organisms. For example, genes of related species encoding enzymes that exhibit the same function are known to cross-hybridize.

Genes according to the present invention are not limited to double-stranded DNA, and may be the sense strand or anti-sense strand of double-stranded DNA or RNA. The anti-sense strand may be used as a probe or anti-sense compound. For DNA, cDNA or genomic DNA obtained by cloning techniques, chemical synthesis techniques, or a combination of these different techniques may be used. Further, genes according to the present invention may include a sequence of an untranslated region (UTR), or a vector sequence (including expression vector sequence).

(3) Proteins According to the Present Invention

[Δ6 Desaturase Protein According to the Present Invention]

A Δ6 desaturase protein according to the present invention is a Marchantiales-derived protein that has a Δ6 fatty acid desaturating activity. Specifically, the protein satisfies the following conditions:

1. A protein encoded by the Δ6 fatty acid desaturase gene of the invention defined in section (2) above;
2. A protein with an amino acid sequence of SEQ ID NO: 2; and
3. A protein with an amino acid sequence that has been modified by substitution, deletion, insertion, and/or addition of one or more amino acids of the amino acid sequence of SEQ ID NO: 2.

[Δ6 Chain Elongase Protein According to the Present Invention]

A Δ6 chain elongase according to the present invention is a Marchantiales-derived protein that has a Δ6 chain elongating activity. Specifically, the protein satisfies the following conditions:

1. A protein encoded by the Δ6 chain elongase gene of the invention defined in section (2) above;
2. A protein with an amino acid sequence of SEQ ID NO: 4; and
3. A protein with an amino acid sequence that has been modified by substitution, deletion, insertion, and/or addition of one or more amino acids of the amino acid sequence of SEQ ID NO: 4.

[Δ5 Desaturase Protein According to the Present Invention]

A Δ5 desaturase protein according to the present invention is a Marchantiales-derived protein that has a Δ5 fatty acid desaturating activity. Specifically, the protein satisfies the following conditions:

1. A protein encoded by the Δ5 fatty acid desaturase gene of the invention defined in section (2) above;
2. A protein with an amino acid sequence of SEQ ID NO: 6; and
3. A protein with an amino acid sequence that has been modified by substitution, deletion, insertion, and/or addition of one or more amino acids of the amino acid sequence of SEQ ID NO: 6.

As the term is used herein, the "Δ6 fatty acid desaturating activity" means that the enzyme has substrate specificity to linoleic acid and α-linolenic acid, and converts these acids to γ-linolenic acid and stearidonic acid, respectively. As the term is used herein, "Δ6 chain elongating activity" means that the enzyme has substrate specificity to γ-linolenic acid and stearidonic acid, and converts these acids to dihomo-γ-linolenic acid and eicosatetraenoic acid, respectively. Further, as the term is used herein, the "Δ5 fatty acid desaturating activity" means that the enzyme has substrate specificity to dihomo-γ-linolenic acid and eicosatetraenoic acid, and converts these acids to arachidonic acid and eicosapentaenoic acid (EPA), respectively.

As used herein, "substitution, deletion, insertion, and/or addition of one or more amino acids" means substitution, deletion, insertion, and/or addition of preferably no more than 10, more preferably no more than 7, and further preferably no more than 5 amino acids, as enabled by a mutant protein producing method known in the art, for example, such as a site-directed mutagenesis inducing method. Such mutant proteins are not limited to those intentionally mutated by a known mutant protein producing method, but also include those prepared by isolating and purifying mutant proteins that exist in nature.

Proteins according to the present invention are not particularly limited as long as they are polypeptides consisting of amino acids forming peptide bonds. For example, the proteins may be conjugated proteins with an additional non-peptide structure. Non-limiting examples of such a non-peptide structure include a sugar chain and isoprenoid group.

Further, proteins according to the present invention may include additional peptides. Examples of such additional peptides include various epitopes such as His, Myc, and Flag tagged to proteins of the present invention.

Further, proteins according to the present invention may be obtained by introducing genes according to the present invention (genes encoding proteins of the present invention) into a host cell and expressing the genes therein. Alternatively, the proteins may be obtained by isolating and purifying from cells or tissues. Further, depending on the expression conditions in the host cell, proteins according to the present invention may be fusion proteins with other proteins. Further, proteins according to the present invention may be chemically synthesized.

(4) Method of Obtaining Proteins and Genes According to the Present Invention

A method of obtaining (producing) proteins and genes according to the present invention is not particularly limited. The following describes some representative methods.

[Method of Obtaining a Protein]

As mentioned above, a method of obtaining (producing) proteins of the present invention is not particularly limited. In one method, proteins according to the present invention are simply purified from cells or tissues expressing the proteins. A purification method is not particularly limited either. For example, a cell extract prepared from cells or tissues by a known method is purified by a known method, using a column for example.

Further, proteins according to the present invention may be obtained by a method employing a genetic engineering technique. In this case, for example, a vector that has incorporated genes of the invention is expressibly introduced into a host cell by a known method, and the proteins obtained by translating the genes in the cell are purified.

An expression vector used to introduce foreign genes into a host is suitably selected from a group of expression vectors that have incorporated different types of promoters that become functional in the host and express the genes. A host is also suitably selected from different types of hosts. For the purification of the proteins, different methods are used depending on the type of host or properties of the proteins used. For example, required proteins can be purified relatively easily with use of a tag.

A method of preparing a mutant protein is not particularly limited either. For example, a mutant protein may be generated by introducing a point mutation in the nucleotide sequence using conventional mutant protein inducing methods, such as a site-directed mutagenesis (see Hashimoto-Gotoh, Gene 152, 271-275 (1995), for example) or PCR. Alternatively, a mutant protein may be generated by a method in which mutant strains are produced by insertion of transposons. Further, a commercially available kit may be used to prepare mutant proteins.

A method of obtaining proteins of the present invention is not limited to the foregoing methods, and a chemical synthesis method may be used. For example, proteins according to the present invention may be synthesized from genes of the present invention, using a cell-free protein synthesis solution.

[Method of Obtaining Genes]

A method of obtaining (producing) genes of the present invention is not particularly limited either. For example, a method employing differential screening (subtraction cloning) may be used. In this method, direct hybridization is repeated in a test tube according to a method known in the art, so as to concentrate required cDNA (genes of the invention).

The differential screening may be carried out in steps under the conditions normally employed. The resulting clones can then be analyzed in detail by creating a restriction enzyme map and by sequencing the clones. By the analysis, the presence or absence of DNA fragments including gene sequences of the present invention can be confirmed.

In another method of obtaining genes of the present invention, DNA fragments including genes of the present invention are isolated and cloned by a known method. For example, a probe is prepared that hybridizes specific to a portion of nucleotide sequences of genes according to the present invention, so as to screen the genomic DNA library or cDNA library. The probe is not particularly limited and may have any sequence or length, as long as it can hybridize specific to at least a portion of nucleotide sequences or their complementary sequences of genes according to the present invention.

When a probe sequence is selected from a region well conserved among different species of Marchantiales, screening of genomic DNA or cDNA of other species of Marchantiales using the probe enables isolation and cloning of genes that encode homologous or analogous molecules functionally similar to proteins of the invention.

Further, in another method of obtaining genes of the present invention, amplifying means such as PCR may be used. For example, primers are prepared from the 5' end and 3' end of a cDNA sequence (or its complementary sequence) of genes according to the present invention. With these primers, PCR is carried out using the genomic DNA (or cDNA) as a template. The PCR amplifies a region of DNA flanked by the primers, thereby producing a large number of DNA fragments including genes of the present invention.

(5) Method of Use (Usefulness) of Genes and Proteins According to the Present Invention (5-1) Recombinant Expression Vector A recombinant expression vector according to the present invention is not particularly limited as long as it includes genes of the present invention described in section (2) above. For example, a recombinant expression vector that has incorporated cDNA may be used. The recombinant expression vector may be prepared using a plasmid, phage, or cosmid as non-limiting examples. Alternatively, the recombinant expression vector may be prepared by a method known in the art.

The type of vector is not particularly limited as long as it is expressed in a host cell. Specifically, such vectors are prepared by introducing genes of the present invention in a plasmid along with promoter sequences that have been suitably selected to ensure gene expression. The promoter sequences depend on the type of host cell.

Various markers may be used to confirm whether genes of the present invention have been introduced in a host cell, or whether the genes have been successfully expressed in the host cell. For example, a marker (a gene lacking in the host cell) is integrated with a carrier, such as a plasmid, together with genes of the present invention, and is introduced into the host cell as an expression vector. Successful uptake of the genes of the present invention may be confirmed by checking the expression of the marker in the host cell that has incorporated the expression vector. Alternatively, protein according to the present invention may be expressed in the form of fusion proteins in the host cell. For example, proteins according to the present invention may be expressed as fusion proteins with a green fluorescent protein (GFP) derived from *Aequorea victoria*. In this case, the GFP is used as a marker.

The host cell is not particularly limited, and various conventionally available cells may be used. Non-limiting examples of such cells include: bacteria such as *Escherichia coli*; yeasts such as *Saccharomyces cerevisiae* or *Schizosaccharomyces pombe*; *Caenorhabditis elegans*; and oocytes of *Xenopus laevis*.

A method of introducing the expression vector into the host cell (method of transformation) is not particularly limited and various conventional methods may be used, including an electroporation method, calcium phosphate method, liposome method, and DEAE dextran method, for example. Further, when proteins of the present invention are transferred and expressed in insects, an expression system using baculovirus may be used.

(5-2) Transformants

Transformants according to the present invention are not particularly limited as long as they incorporate genes of the present invention described in section (2) above. As the term is used herein, "transformants" means not only cells, tissues, or organs, but also living organisms themselves.

A method of preparing (producing) transformants is not particularly limited. For example, a host cell may be transformed by introducing a recombinant expression vector described above. The organisms to be transformed are not particularly limited, and may be microorganisms or animals as exemplified above.

Further, transformants according to the present invention are preferably plants into which genes of the present invention are expressibly introduced, or their progeny or vegetatively propagated plants having the same characteristics. Preferably, tissues of these plants also fall within the meaning of "transformants." With these transformant plants, polyunsaturated fatty acids such as arachidonic acid and EPA can be produced at low cost by an environmentally friendly process.

Further, as used herein, "expressibly introduce genes" means that genes are expressibly introduced into a target cell (host cell), using known genetic engineering (gene manipulation) techniques.

The recombinant expression vector used for the transformation of plants is not particularly limited as long as it can express the inserted genes in the plant cell. Examples of such a vector include a vector with a promoter (for example, cauliflower mosaic virus 35S promoter) for constitutively expressing genes in a plant cell, and a vector with a promoter that is inductively activated in response to external stimuli. Here, the plant cells include various types of plant cells, for example, such as cells in a suspension culture, protoplasts, slices of leaves, and calluses.

The recombinant expression vector may be introduced into a plant cell by a method known in the art, for example, such as a polyethylene glycol method, electroporation method, a method using *Agrobacterium*, and a particle gun method. Reproduction of plants from the transformed cells may be carried out by a method known in the art.

For example, there have been established methods of obtaining transformed tobacco, including: a method in which a transformed *Agrobacterium* is used to infect a tobacco leaf disc; a method in which genes are introduced into a protoplast using polyethylene glycol to reproduce plants; a method in which genes are introduced into a protoplast by an electrical pulse to reproduce plants; and a method in which genes are directly introduced into a cell by a particle gun method to reproduce plants. The present invention can suitably employ any of these methods.

Further, beside *Arabidopsis thaliana*, tobacco is also a model plant of plant cultivation using genetic engineering techniques. Once a transformant tobacco with a high arachidonic acid or EPA content is obtained, it will be possible to obtain such transformants in all other plants. In addition to transformant tobacco, the present invention also provides transformant rice, as will be described later in Examples. Therefore, the invention is able to provide transformants in any type of plant.

For example, there have been established methods of obtaining transformed rice, including: a method in which genes are introduced into a protoplast using polyethylene glycol to reproduce plants; a method in which genes are introduced into a protoplast by an electrical pulse to reproduce plants; and a method in which genes are directly introduced into a cell by a particle gun method to reproduce plants. The present invention can suitably employ any of these methods.

With a transformant rice containing an increased level of arachidonic acid or EPA, intake of these and other polyunsaturated fatty acids is possible only by eating the seeds (grains) of the transformant. Therefore, the transformant rice is highly valuable as a food crop, and is highly useful in food industries and agricultures. Further, arachidonic acid or EPA can also be produced in rice bran, chaff, or tiller, which are often wasted. By extracting fatty acids from these parts of plant, they can be efficiently used as a source of health food. They can also be used as food of domestic animals.

Once a transformant plant is obtained that has incorporated genes of the present invention in its genome, progeny of the plant can be obtained by reproducing the plant either sexually or asexually. Further, reproductive materials, for example, such as seeds, fruits, cuttings, tuberous stems, tuberous roots, stumps, callus, and protoplasts may be obtained from the plant, or from its progeny or clones. From these reproductive materials, the plant may be mass produced. The present invention therefore includes plants into which genes of the invention are expressibly introduced, their progeny or vegetatively propagated plants having the same characteristics, tissues of the plants, and reproductive materials of the plants. Further, the plants, their progeny or vegetatively propagated plants having the same characteristics, and tissues of the plants include plants that are reproduced vegetatively. Vegetative reproduction is also known as vegetative generation or clonal expansion, and is commonly carried out by making a plant or herbaceous cutting. In a test tube, vegetative reproduction of plants may be carried out by redifferentiating plants from such organs as the leaf, stem, or root, or by using a callus. In some plant species, a unique winter bud may form at the tip of a branch, or a succulent axillary bud may be formed. In other cases, flowers may form a propagule, or a tuber may be formed.

Further, the present invention includes plants into which genes of the present invention are expressibly introduced, and whose fatty acid composition is modified by the expression of the genes. The invention also includes their progeny or vegetatively propagated plants having the same characteristics, tissues of the plants, and reproductive materials of the plants. As used herein, "modification of fatty acid composition" means altering of a fatty acid composition of plant by way of transformation. For example, such a change can be induced by introducing genes of the present invention to transform a plant which does not contain arachidonic acid or EPA in its fatty acid composition. This will change the fatty acid composition of the plant by the production of arachidonic acid and EPA.

(5-3) Fatty Acid Producing Method

The present invention includes a producing method of fatty acids, using a plant that has been transformed by genes of the present invention and thereby whose fatty acid composition has been modified, or using tissues of the plant.

For example, food oil may be produced from a transformant according to the present invention containing a high level of arachidonic acid or EPA. With the increased level of arachidonic acid or EPA, the value of the product food oil can be increased. Further, various parts of the transformant plant, for example, such as seeds, fruits, cuttings, tuberous stems, and tuberous roots, can be used to supply arachidonic acid- or EPA-containing food with an increased value.

(5-4) Material Substance

The present invention includes a substance obtained by a fatty acid producing method of the invention. Specifically, the invention includes a material substance which includes at least one compound selected from the group consisting of: γ-linolenic acid, dihomo-γ-linolenic acid, arachidonic acid, stearidonic acid, eicosatetraenoic acid, and eicosapentaenoic acid. As used herein, "material substance" means all substances usable as raw materials for various industrial purposes, including seeds, fruits, cuttings, tuberous stems, and tuberous roots, provided as food.

A material substance containing arachidonic acid or EPA may be used to provide health food, film, biodegradable plastic, functional fiber, lubricant, and detergent, for example. The polyunsaturated fatty acids have a unique property of containing more than one double bond within the molecule. Thus, by producing arachidonic acid or EPA in a transformant of the present invention for example, production cost can be reduced. Further, the invention realizes an environmentally friendly producing process.

(5-5) Fatty Acid Composition Modifying Method

The present invention includes a method of modifying a fatty acid composition using genes of the present invention. For example, with a transformant that has incorporated genes of the present invention as above, a fatty acid composition of the host cell can be modified. A target organism of fatty acid composition modification is not particularly limited. Other than plants, any organism may be used, including animals, microorganisms, and yeasts.

(5-6) Gene Detecting Instrument

A gene detecting instrument according to the present invention includes at least a portion of a nucleotide sequence, or its complementary sequence, of a gene of the present invention as a probe. The gene detecting instrument of the invention can be used, under various conditions, for the measurement or detection of expression pattern of genes according to the present invention.

An example of a gene detecting instrument according to the present invention is a DNA chip in which a probe that hybridizes specific to genes of the present invention is immobilized on a substrate (carrier). As used herein, the term "DNA chip" generally means a synthetic DNA chip using a synthetic nucleotide as a probe, but the "DNA chip" also means an adhesion DNA microarray that uses a PCR product, such as cDNA, as a probe.

The probe sequence may be determined by a conventional method of specifying a characteristic sequence of cDNA sequences. For example, a SAGE (Serial Analysis of Gene Expression) method, as described in Science 276:1268, 1997; Cell 88: 243, 1997; Science 270: 484, 1995; Nature 389: 300, 1997; U.S. Pat. No. 5,695,937 may be used.

The DNA chip may be made by a conventional method. For example, when a synthetic oligonucleotide is used, it may be synthesized on a substrate by a combination of photolithography and solid phase DNA synthesis technique. On the other hand, when the oligonucleotide is cDNA, it is stuck on a substrate using an array device.

Further, as in common DNA chips, the accuracy of gene detection can be improved by placing a perfect-match probe (oligonucleotide) with a mismatch probe that has been prepared by substituting a single nucleotide of the perfect-match probe. Further, in order to detect different genes simultaneously, a DNA chip may be prepared in which different types of oligonucleotides are immobilized on a single substrate.

A gene detecting instrument of the present invention is not just limited to the DNA chip as exemplified above, as long as it uses at least a portion of a nucleotide sequence, or its complementary sequence, of a gene of the present invention as a probe.

(5-7) Antibody

An antibody according to the present invention is a polyclonal or monoclonal antibody obtained by a method known in the art, using proteins of the invention, or fragments of the proteins or peptides as an antigen. Examples of the conventional method include Harlow et al.; Antibodies: A laboratory manual (Cold Spring Harbor Laboratory, New York (1988), and Iwasaki et al.; Monoclonal antibody, hybridoma and ELIZA, Kodansha (1991). The antibody may be used in the detection and/or measurement of a protein according to the present invention.

(5-8) Screening Method

A screening method according to the present invention uses proteins of the present invention to screen for genes or substances that regulate the proteins. A screening method of the invention is not particularly limited, and a variety of conventional methods that find the presence or absence of bonding or dissociation between substances may be used. For example, substances that facilitate the activities of proteins according to the present invention (Δ6 desaturase activity, Δ6 chain elongase activity, and/or Δ5 desaturase activity) may be screened.

The present invention also includes genes or proteins obtained by such a screening method.

While the invention is susceptible to various modifications and alternative forms, a specific embodiment thereof will be described below in more detail by way of Examples with reference to the attached drawings. It should be understood, however, that it is not intended to limit the invention to the particular forms disclosed, but on the contrary, the invention is to cover all modifications, equivalents, and alternatives falling within the scope of the invention as defined in the appended claims.

EXAMPLES

In the following Examples, experimental methods, unless otherwise specified, are based on the method described in Molecular Cloning (Sambrook et. al. Cold Spring Harbour Laboratory Press, 1989).

Example 1

Isolation of *Marchantia polymorpha*-derived Δ6 Desaturase Gene

A comparison of amino acid sequences of cloned Δ6 desaturases has confirmed that the amino acid sequences Trp-Trp-Lys-(Glu/Asp)-Lys-His-Asn (SEQ ID NO: 37) and Trp-Phe-Thr-Gly-Gly-Leu-Asn (SEQ ID NO: 38) were conserved. To isolate a *Marchantia polymorpha*-derived Δ6 desaturase gene, the following degenerate primers encoding the above amino acid sequences were used:

```
dΔ6DES-F:
                                           (SEQ ID NO: 7)
5'-TGGTGGAA(A/G)GA(A/G/T/C)AA(A/G)CA(T/C)AA-3';
and dΔ6DES-R:
                                           (SEQ ID NO: 8)
5'-(A/G)TTIA(A/G)ICCICCIGT(A/G)AACCA-3'.
("I" denotes inosine, and more than one nucleotide exist in
parentheses.)
```

A thallus of E-line *Marchantia polymorpha* (see Transgenic Res. 9, p179, 2000) was used as a sample. Isolation of poly(A)+ RNA from the thallus was carried out in accordance with the method described in Biosci. Biotechnol. Biochem. 67, p605, 2003; Biosci. Biotechnol. Biochem. 67, p1667, 2003. 1.5 µl of isolated poly(A)+ RNA was reverse-transcribed to cDNA using a Ready-To-Go T-primed First Strand kit (Amersham). PCR was carried out with about 10 ng of the cDNA as a template, using the foregoing primers (dΔ6DES-F and dΔ6DES-R) and 0.5 U of enzyme (Takara Ex Taq, Takara), by a method recommended by the manufacturer. Using a GeneAmp PCR system 9700 (PE Applied Biosystems), the PCR was carried out with 20 µl of a reaction solution under the following conditions: 94° C. for 2 minutes, followed by 35 cycles of reaction at 94° C. for 1 minute, 45° C. for 1.5 minutes, and 72° C. for 2 minutes, and cooling down to 4° C.

The resulting PCR product was electrophoresed on a 1% (w/v) agarose gel, and amplified fragments having a size expected from a known amino acid sequence of a conventional Δ6 desaturase was collected from the gel using a Prep-A Gene (Bio-rad). The collected fragments were ligated to a pT7Blue Vector (Takara) and transformed into *Escherichia coli* Electro-max DH10B cells (Invitrogen, Carlsbad, Calif.).

Nucleotide sequences of all clones obtained by a BigDye Terminator Cycle Sequencing kit (Applied Biosystems) and an automated sequencer ABI PRISM 377 (Applied Biosystems) were determined, and the clones were screened for a target cDNA sequence.

Further, to obtain a full-length cDNA sequence, 5'-RACE and 3'-RACE were carried out by a method recommended by the manufacturer, using a 5'-RACE System for Rapid Amplification of cDNA Ends Version 2.0 (Invitrogen), a Ready-To-Go T-primed First Strand kit (Amersham), and the following primers:

```
MpDES6-02R:
                                           (SEQ ID NO: 9)
5'-AAGTTGCCTTCGATGTTTCTGG-3';
and MpDES6-01F:
                                           (SEQ ID NO: 10)
5'-GCTCGCCTGGAGCAAGGAAATC-3'.
```

As a result, one type of candidate homologue gene was isolated as an MpDES6 gene. The length of cDNA (not including a poly(A) portion) of the isolated MpDES6 gene was 2,522 bp, and an amino acid sequence encoded by the MpDES6 gene was estimated to have 481 residues. The nucleotide sequence and amino acid sequence of the MpDES6 gene are represented by SEQ ID NO: 1 and SEQ ID NO: 2, respectively.

A comparison between the estimated amino acid sequence of MpDES6 cDNA and an amino acid sequence of Δ6 desaturase from *Physcomitrella patens* found only 47.5% identity.

Example 2

Isolation of *Marchantia polymorpha*-Derived Δ6 Chain Elongase Gene

A comparison of amino acid sequences of cloned Δ6 chain elongases has confirmed that the amino acid sequences Val-Glu-Phe-Met-Asp-Thr-Val (SEQ ID NO: 39) and Lys-Tyr-Leu-Phe-Trp-Gly-Arg (SEQ ID NO: 40) were conserved. To isolate a *Marchantia polymorpha*-derived Δ6 chain elongase gene, the following degenerate primers coding for the above amino acid sequences were used:

```
dΔ6ELO-F:
                                           (SEQ ID NO: 11)
5'-GTIGA(A/G)TT(T/C)ATGGA(T/C)ACIGT-3';
and dΔ6ELO-R:
                                           (SEQ ID NO: 12)
5'-C(G/T)ICCCCA(A/G)AAIA(A/G)(A/G)TA(T/C)TT-3'.
```

PCR was carried out using the these primers (dΔ6ELO-F and dΔ6ELO-R), and the resulting DNA fragments were subcloned. Nucleotide sequences of the clones were determined, and a full-length cDNA was obtained for clones that had a target cDNA sequence, using the following primers:

```
MpELO1-02R:
                                        (SEQ ID NO: 13)
5'-GCGAGCTTTCTCGTTCTTTCCC-3';
and MpELO1-01F:
                                        (SEQ ID NO: 14)
5'-TATGATTTTGAAGCGCAACACG-3'.
```

Note that, the materials and methods for the experiment were the same as for Example 1.

As a result, one type of candidate homologue gene was isolated as an MpELO1 gene. The length of cDNA (not including a poly(A) portion) of the isolated MpELO1 gene was 1,559 bp, and an amino acid sequence encoded by the MpDES1 gene was estimated to have 290 residues. The nucleotide sequence and amino acid sequence of the MpDES1 gene were represented by SEQ ID NO: 3 and SEQ ID NO: 4, respectively.

A comparison between the estimated amino acid sequence of MpELO1 cDNA and an amino acid sequence of Δ6 chain elongase from *Physcomitrella patens* found 62.7% identity.

Example 3

Isolation of *Marchantia polymorpha*-Derived Δ5 Desaturase Gene

The Δ5 desaturases of other species have a cytochrome b5 domain at their N-terminus. From this, it was speculated that a *Marchantia polymorpha*-derived Δ5 desaturase gene belongs to a cytochrome b5-domain fusion desaturase gene family, as does the Δ6 desaturase gene. However, in *Phaeodactylum tricornutum* and fungi, the homology between the Δ5 desaturase and Δ6 desaturase is very poor at an amino acid level. As such, amino acid sequences of the Δ5 desaturase and Δ6 desaturase were compared in a filamentous fungus (*M. alpina*). The comparison found local presence a contiguous conserved sequence of 4 to 5 residues, which is at least required for the designing of degenerate primers. Surprisingly, the amino acid sequences were more conserved between the Δ5 desaturase and Δ6 desaturase of the same species than between Δ5 desaturases obtained from different species. This suggests the presence of a species-specific conserved sequence in the cytochrome b5-domain fusion desaturase gene. To investigate on this, the nucleotide sequences of the MpDES6 and the MpDES of an unknown function, described in Genetics 159, p981, 2001, were compared. As a result, it was found that two amino acid sequences: (I(E/N)(G/D)KVYDV (SEQ ID NO: 41) and DPDI(Q/D)(Y/T)(M/V)P (SEQ ID NO: 42)) were conserved. Sequences of degenerate primers corresponding to the respective amino acid sequences are as follows:

```
dΔ5DES-F:
                                        (SEQ ID NO: 15)
5'-AT(A/T/C)(A/G)AIG(A/G)IAA(A/G)TITA(T/C)GA
(T/C)GT-3';
and dΔ5DES-R:
                                        (SEQ ID NO: 16)
5'-GGIA(T/C)I(G/T)(A/T)IT(G/C)(A/G/T)AT(A/G)TCIGG
(A/G)TC-3'.
```

PCR was carried out using these primers (dΔ5DES-F and dΔ5DES-R), and the resulting DNA fragments were subcloned. Nucleotide sequences of the clones were determined, and a full-length cDNA was obtained for clones that had a target cDNA sequence, using the following primers:

```
MpDES5-02R:
                                        (SEQ ID NO: 17)
5'-GTGTGTACGATCCGTGGTTACC-3';
and MpDES5-01F:
                                        (SEQ ID NO: 18)
5'-AAGGCGGGACAGGATTCAACAC-3'.
```

Note that, the materials and methods for the experiment were the same as for Example 1.

From the cDNA, clones c1 and c2 of different lengths (c1: 2,427 bp; c2: 2,285 bp) were isolated as candidates for the *Marchantia polymorpha*-derived Δ5 desaturase gene. By comparing the nucleotide sequences of the clones c1 and c2, it was found that alternative splicing had occurred in a 5' non-coding region. The alternative splicing did not change the reading frame, and both clones c1 and c2 coded for 484 amino acids (SEQ ID NO: 6). The clone c1 of 2,427 by was used as a MpDES5 gene (SEQ ID NO: 5) in the following Examples.

A comparison of an estimated amino acid sequence of MpDES5 cDNA with an amino acid sequence of the Δ5 desaturase of a filamentous fungus (*M. alpina*) found 31.4% identity. No comparison was made for the Δ5 desaturase of *Physcomitrella patens*, which is closely related to *Marchantia polymorpha*, because no sequence information is available for the Δ5 desaturase of this particular organism.

Example 4

Functional Analysis Using Methylotrophic Yeast (*Pichia pastoris*)

To examine functions of the respective cDNAs of the MpDES6, MpELO1, and MpDES5, a construct in which an ORF was placed downstream of a methanol-inducible promoter AOX1 was prepared for each gene. The constructs were introduced into methylotrophic yeast (*Pichia pastoris*) to analyze their fatty acid compositions. The ORFs of cDNA nucleotide sequences of the MpDES6, MpELO1, and MpDES5 were PCR-amplified using the following primers.

```
(Primers for the amplification of MpDES6 ORF)
MpD6-17F:
                                        (SEQ ID NO: 19)
5'-GGAATTCGCGATGGCCTCGTCCACCACCAC-3';
and MpD6-18F:
                                        (SEQ ID NO: 20)
5'-GGAATTCTACTTTCGCAGCGTATGCTACC-3'.

(Primers for the amplification of MpELO1ORF)
MpD6ELO1-15F:
                                        (SEQ ID NO: 21)
5'-GGAATTCGCGATGGAGGCGTACGAGATGG-3';
and MpD6ELO1-16F:
```

-continued (SEQ ID NO: 22)
5'-GGAATTCTTCTGCCTTTTTGCTCTTGATC-3'.

(Primers for the amplification of MpDES5 ORF)
MpD5-11F:
(SEQ ID NO: 23)
5'-GTTGAATTCGACAGTTATGCCGCCACACGC-3';
and MpD5-12R:
(SEQ ID NO: 24)
5'-GTTGAATTCAGGCCCAAAGCATGCTGTCAC-3'.

These primers contained EcoRI recognition sequences (underlined) and were used in the following cloning process. Further, PCR was carried out using 0.5 U of Pyrobest DNA polymerase (Takara) with 20 μl of reaction solution, in accordance with the method recommended by the manufacturer. The reaction condition was as follows: 94° C. for 2 minutes, followed by 25 cycles of reaction at 94° C. for 1 minute, 57° C. for 1 minute, and 72° C. for 1 minute, and cooling down to 4° C. Each of the resulting ORF fragments was digested with EcoRI, gel purified by the method described in Example 1, and ligated in the sense direction to an EcoRI site downstream of a methanol-inducible promoter 5'AOX1 in a methylotrophic yeast expression vector pPICZA (Marker: zeocin-resistant gene, Invitrogen).

In order to obtain transformants, expression constructs and a pPICZA vector as a control were introduced into a PPY1-line of methylotrophic yeast using a *Pichia* EasyComp kit (Invitrogen), using a zeocin-resistant gene as a marker. Note that, the methylotrophic yeast can synthesize linoleic acid and α-linolenic acid, which are substrates of the Δ6 desaturase, but cannot synthesize other precursors of arachidonic acid or EPA.

To express the introduced genes in the transformants, the transformants were first cultured until OD (600 nm) became 0.5 in a minimal medium containing 1.0% glycerol as a sole carbon source. The transformants were then cultured at 30° C. for three days in a minimal medium containing 0.5% methanol as a sole carbon source, until saturation was reached. Here, an EasySelect *Pichia* Expression Kit (Invitrogen) was used according to the method recommended by the kit. Thereafter, fatty acid compositions of the respective transformants were measured using a GC-MS and according to a known method (Biosci. Biotechnol. Biochem. 67, p605, 2003).

In an MpDES6 gene-expressing transformant, the products of the Δ6 desaturase reaction, γ-linolenic acid and stearidonic acid, were contained in 7.4% and 0.7%, respectively, with respect to the total fatty acids. In a pPICZA vector-introduced yeast used as a control, γ-linolenic acid and stearidonic acid were not detected. Thus, it was shown that the MpDES6 encoded the Δ6 desaturase.

In an MpELO1 gene-expressing transformant, 14.1% of the total fatty acids was dihomo-γ-linolenic acid when γ-linolenic acid was added. On the other hand, 1.5% of the total fatty acids was eicosatetraenoic acid when stearidonic acid was added. In a pPICZA vector-introduced yeast used as a control, dihomo-γ-linolenic acid or eicosatetraenoic acid was not detected. Thus, it was shown that the MpELO1 encoded the Δ6 chain elongase.

In an MpDES5 gene-expressing transformant, 1.1% of the total fatty acids was arachidonic acid when dihomo-γ-linolenic acid was added. On the other hand, 0.1% of the total fatty acids was eicosapentaenoic acid (EPA) when stearidonic acid was added. In a pPICZA vector-introduced yeast used as a control, arachidonic acid or eicosapentaenoic acid was not detected. Thus, it was shown that the MpDES5 encoded the Δ5 desaturase.

It was therefore confirmed that Marchantia polymorpha can be used to obtain MpDES6, MpELO1, and MpDES5, which are genes that encode the Δ6 desaturase, Δ6 chain elongase, and Δ5 desaturase, respectively.

Example 5

Reconstruction of *Marchantia polymorpha* Polyunsaturated Fatty Acid Biosynthesis System in a Methylotrophic Yeast (*P. pastoris*)

To co-express the MpDES6, MpELO1, and MpDES5, EcoRI-digested amplified ORF fragments of MpELO1 and MpDES5 prepared in Example 4 were ligated to a methylotrophic yeast-expression vector pPIC3K (Marker: HIS4 gene, Invitrogen) and a methylotrophic yeast-expression vector PIC6A (Marker: blasticidin-resistant gene, Invitrogen), respectively. In each vector, the ligation was made in the sense direction at the EcoRI site downstream of a 5'AOX1 promoter. For the MpDES6, the expression vector prepared in Example 4 was used. Hereinafter, the expression vectors for the MpDES6, MpELO1, and MpDES5 are referred to as pPICZA-MpDES6 vector, pPIC3K-MpELO1 vector, and pPIC6A-MpDES5 vector, respectively.

The pPICZA-MpDES6 vector was transferred into a methylotrophic yeast PPY12 line (his4, arg4) having the same fatty acid composition as the methylotrophic yeast PPY1 used in Example 4. As a control, a pPICZA vector was also transferred. Transformants were obtained using a zeocin-resistance marker. Then, the pPIC3K-MpELO1 vector was introduced into the transformant that has incorporated the pPICZA-MpDES6 in its genome and the transformant that has incorporated the pPICZA in its genome. The pPIC3K vector was also introduced as a control into the transformants in the same manner. Transformants were obtained using the histidine synthesizing ability as a marker. Finally, the pPIC6A-MpDES5 vector was introduced into the transformant that has incorporated the pPICZA-MpDES6 and pPIC3K-MpEL01 in its genome, and to the transformant that has incorporated the pPICZA and pPIC3K in its genome. The pPIC6A vector was also introduced as a control into the transformants in the same manner. Transformants were obtained using the blasticidin resistance as a marker.

Using the transformants that have incorporated two or three kinds of genes, an experiment was conducted to reconstruct the arachidonic acid/EPA biosynthesis system of *Marchantia polymorpha*. First, using the transformants that have incorporated the two types of genes (MpDES6 and MpELO1), an MpDES6 gene and an MpELO1 gene were co-expressed in the methylotrophic yeasts. As a result, γ-linolenic acid and stearidonic acid, which are the products of Δ6 desaturation, were contained in 2.9% and 0.4%, respectively, with respect to the total fatty acids, whereas dihomo-γ-linolenic acid and eicosatetraenoic acid, which are produced by the chain elongation of the γ-linolenic acid and stearidonic acid, respectively, were contained in 2.8% and 0.2%, respectively, with respect to the total fatty acids. in the controls, these fatty acids were not detected, In the transformants that have incorporated three types of genes (MpDES6, MpELO1, and MpDES5), production of arachidonic acid (0.1% in the total fatty acids) and eicosapentaenoic acid (EPA, 0.03% in the total fatty acids) was confirmed, in addition to the γ-linolenic acid, stearidonic acid, dihomo-γ-linolenic acid, and eicosatetraenoic acid, which were contained in 2.8%, 0.5%, 1.5%, and 0.1%, respectively, with respect to the total fatty acids. In the controls, these fatty acids were not detected. This result showed that reconstruction of polyunsaturated fatty acid biosynthesis system is indeed possible in organisms other than *Marchantia polymorpha*, by expressing *Marchantia polymorpha*-derived Δ6 desaturase gene, Δ6 chain elongase gene, and Δ5 desaturase gene therein.

Example 6

Construction of a Vector for Rice, and Transfer of the Vector into Rice

To express the MpDES6 gene, MpELO1 gene, and MpDES5 gene in rice, expression constructs were prepared in the following steps (i) to (iv). FIG. 1 shows the procedure.

In PCR using primers that were designed between a cauliflower mosaic virus (CaMV) 35S promoter and a NOS terminator of pBI221 (TOYOBO), an expression vector p35S—NOS not including a β-Glucuronidase (GUS) gene portion was prepared.

Namely, the following primers were used in PCR:

```
MK001(F):
                                        (SEQ ID NO: 25)
5'-CGGGATCCTCTCCTGGCGCACCATCGTC-3';
and MK002(R):
                                        (SEQ ID NO: 26)
5'-GGGGTACCAACGCGCTTTCCCACCAACG-3'.
```

Note that, the primer MK001(F) contained a BamHI recognition sequence (underlined) and was annealed to the 3' end of the GUS gene. The primer MK002(R) was annealed to the 5' end of the GUS gene. (BamHI site is upstream of the annealed site.) The PCR was carried out with 50 μl of reaction solution, using 0.5 U of Pyrobest DNA polymerase (Takara) by the method recommended by the manufacturer. The reaction conditions were as follows: 96° C. for 5 minutes, followed by 30 cycles of reaction at 94° C. for 30 seconds and 68° C. for 4 minutes, and cooling down to 4° C. The resulting ORF fragments were digested with BamHI, gel purified by the method described in Example 1, and were self-ligated.

(ii) Next, the ORFs of the MpDES6 gene, MpELO1 gene, and MpDES5 gene were ligated to the XbaI site of p35S—NOS. For the amplification of ORFs, the following primers containing an XbaI recognition sequence (underlined) were used.

```
(Primers for the amplification of MpDES6 ORF):
MpD6-21F:
                                        (SEQ ID NO: 27)
5'-GCTCTAGAGCGATGGCCTCGTCCACCACC-3';
and MpD6-11R:
                                        (SEQ ID NO: 28)
5'-GCTCTAGACTATACTTTCGCAGCGTATGC-3'.

(Primers for the amplification of MpELO1 ORF):
MpD6ELO1-18F:
                                        (SEQ ID NO: 29)
5'-GCTCTAGAGCGATGGAGGCGTACGAGATGG-3';
and MpD6ELO1-13R:
                                        (SEQ ID NO: 30)
5'-GCTCTAGATTATTCTGCCTTTTTGCTC-3'.

(Primers for the amplification of MpDES5 ORF):
MpD5 22F:
                                        (SEQ ID NO: 31)
5'-GCTCTAGAGACAGTTATGCCGCCACACGC-3';
and MpD5 23R:
                                        (SEQ ID NO: 32)
5'-GCTCTAGAAGGCCCAAAGCATGCTGTCAC-3'.
```

The PCR was carried out with 20 μl of reaction solution, using 0.5 U of Pyrobest DNA polymerase (Takara) by the method recommended by the manufacturer. The reaction conditions were as follows: 94° C. for 2 minutes, followed by 25 cycles of reaction at 94° C. for 1 minute, 57° C. for 1 minute, and 72° C. for 1 minute, and cooling down to 4° C. The resulting ORF fragments were digested with XbaI, gel-purified by the method described in Example 1, and were used for cloning.

(iii) By taking advantage of the fact that all of the resulting gene-expression constructs (respectively represented by p35S-MpDES6, p35S-MpELO1, and p35S-MpDES5) had a PstI site at the 5' end of the CaMV35S promoter and an EcoRI site at the 3' end of the NOS terminator, expression cassettes for these three genes were ligated to one another. First, PCR was carried out using the primers below, and a p35S-MpDES5 as a template, so as to amplify an expression cassette portion of the MpDES5 gene. The amplified fragment was then cloned into the PstI site at the 5' end of the CaMV35S promoter of the p35S-MpDES (see FIG. 1).

```
(Primers for the amplification of MpDES5-gene
expression cassette)
M13R:
                                        (SEQ ID NO: 33)
5'-CAGGAAACAGCTATGACC-3';
and NOS-R4-PST:
                                        (SEQ ID NO: 34)
5'-AAACTGCAGATTCCCGATCTAGTAACATAG-3'.
```

Note that, the M13R primer was annealed to a vector sequence upstream of the CaMV35S promoter. Further, the NOS-R4-PST primer contained a PstI recognition sequence (underlined) and was annealed to the 3' end of the NOS terminator. The EcoRI site at the 3' end of the NOS terminator was not contained.

The PCR was carried out with 20 μl of reaction solution, using 0.5 U of Pyrobest DNA polymerase (Takara) by the method recommended by the manufacturer. The reaction conditions were as follows: 94° C. for 2 minutes, followed by 25 cycles of reaction at 94° C. for 1 minute, 57° C. for 1 minute, and 72° C. for 1 minute, and cooling down to 4° C. The resulting DNA fragments were digested with PstI, gel-purified by the method described in Example 1, and cloned into the PstI site of the plasmid (p35S-MpDES6) containing the MpDES6-gene expression cassette.

(iv) To the resulting construct in which the expression cassettes of the MpDES5 gene and MpDES6 gene were ligated (represented by "p35S-MpDES5/35S-MpDES6"), an expression cassette of the MpELO1 gene was further ligated. PCR was carried out using the primers below, and a p35S-MpELO1 as a template, so as to amplify an expression cassette portion of the MpELO1 gene. The amplified fragment was then cloned into the EcoRI site at the 3' end of the NOS terminator in the MpDES6-gene expression cassette.

(Primers for the amplification of MpELO1-gene expression cassette)
35S-F3-EI:
(SEQ ID NO: 35)
5'-CCG<u>GAATTC</u>GCATGCCTGCAGGTCCCCAGA-3';
and

M13F:
(SEQ ID NO: 36)
5'-TGTAAAACGACGGCCAGT-3'.

Note that, the 35S—F3-EI primer contained an EcoRI recognition sequence (underlined) and was annealed to the 5' end of the CaMV35S promoter. Further, the M13F primer was annealed to a vector sequence downstream of the NOS terminator.

The PCR was carried out with 20 µl of reaction solution, using 0.5 U of Pyrobest DNA polymerase (Takara) by the method recommended by the manufacturer. The reaction conditions were as follows: 94° C. for 2 minutes, followed by 25 cycles of reaction at 94° C. for 1 minute, 57° C. for 1 minute, and 72° C. for 1 minute, and cooling down to 4° C. The resulting DNA fragments were digested with EcoRI, gel-purified by the method described in Example 1, and cloned into the EcoRI site of the construct (p35S-MpDES5/35S-MpDES6) in which the MpDES5-gene expression cassette and the MpDES6-gene expression cassette were ligated.

By these procedure, an expression construct (p35S-MpDES5/35S-MpDES6/p35S-MpELO1) was prepared in which the three genes-expression cassettes of MpDES5, MpDES6, and MpELO1 were ligated in this order.

The construct so obtained was introduced into rice, together with a plasmid having bialaphos as a selection marker, using a particle gun by a known method (Genes Genet. Syst. 73, p219, 1998). As a result, a transformed rice was obtained.

Example 7

Reconstruction of *Marchantia polymorpha* Polyunsaturated Fatty Acid Synthesis System in Tobacco (*N. tabacum* SR-1)

This Example confirmed that the foregoing Marchantia polymorpha-derived unsaturated fatty acid synthetase genes, i.e. the MpDES6 gene, MpDES5 gene, and MpELO1 gene were indeed well functional in plants.

More specifically, by introducing the MpDES6 gene, MpDES5 gene, and MpELO1 gene into tobacco, production of arachidonic acid and other fatty acids were confirmed. For comparison, a tobacco was prepared into which filamentous fungus (M. alpina)-derived Δ6 desaturase gene (MaDES6), Δ5 desaturase gene (MaDES5), and Δ6 fatty-acid-chain elongase (MaELO) were introduced.

(i) Construction of a Vector (pSPB1519) Containing Filamentous Fungus-Derived Genes The pE2113 (Mitsuhara et al. Plant Cell Physiol. 37, 45-59 1996) has a cauliflower mosaic virus 35S (E1235S) promoter, having repeating enhancer sequences, and a nopaline synthase (nos) terminator.

The pE2113 was digested with SnaBI and then ligated to an XhoI linker (TAKARA) to obtain a plasmid. The resulting plasmid was digested with SacI, blunted, and ligated to a BamHI linker (TAKARA) to obtain pUE7. Of the DNA fragments obtained by the digestion of pUE7 with HindIII and EcoRI, a fragment having an E1235S promoter was ligated to a plant-transformation binary vector pBINPLUS (van Engelen et al. Transgenic research 4, p288, 1995) digested with HindIII and EcoRI. As a result, pSPB505 was obtained.

Meanwhile, a plasmid pMLD101 containing the MaDES6 gene was digested with XhoI followed by partial digestion with BamHI, so as to obtain an about 1.6 kb DNA fragment. The DNA fragment so obtained was ligated to a DNA fragment of a binary vector obtained by the digestion of pSPB505 with XhoI and BamHI. As a result, pSPB559 was obtained.

The pUCAP (van Engelen et al. Transgenic research 4, p288, 1995) was digested with AscI, blunted, and ligated to a PacI linker to obtain pUCAPP.

The pE2113 was digested with SnaBI and ligated to a BamHI linker (TAKARA) to obtain pUE6. This pUE6 was digested with SacI, blunted, and ligated to a SalI linker (TAKARA) to obtain pUE8. Of the DNA fragments obtained by the digestion of pUE8 with HindIII and EcoRI, a fragment having an E1235S promoter was inserted into the HindIII-EcoRI site of pUCAPP. A DNA fragment obtained by the digestion of this plasmid with BamHI and SalI was ligated to a DNA fragment obtained by the digestion of cDNA of the MaELO gene with BamHI and XhoI, so as to obtain pSPB1130. The pSPB1130 was digested with PacI, and the resulting DNA fragment of about 2.3 kb was inserted into a PacI site of pBINPLUS. A plasmid having the same transcription direction for the MaELO gene and the nptII gene on the pBINPLUS were selected as pSPB1157P.

Further, the pSPB599 was digested with PacI, blunted, and an AscI linker was inserted to prepare pSPB599A. The pSPB599A was digested with AscI, and a DNA fragment containing the MaDES6 gene, obtained from the digestion of pSPB599A with AscI, was inserted into the AscI site of pSPB1157P to obtain pSPB1157.

An about 1.3 kb DNA fragment obtained from the digestion of pCGP1364 (Plant Cell Physiol. 36, p1023, 1995) with HindIII and SacII was ligated to an about 2.9 kb DNA fragment obtained by digesting pCGP1364 with PstI, blunting it, and digesting it with SacII. These DNA fragments were further ligated to an about 2.7 kb DNA fragment obtained by digesting pUCAPA with SacI, blunting it, and digesting it with HindIII. As a result, pSPB184 was obtained.

Meanwhile, from a pCRII vector into which the MaDES5 gene was subcloned, a DNA fragment containing the MaDES5 gene was excised by digesting with XbaI and KpnI. The resulting DNA fragment was ligated to a DNA fragment obtained by the digestion of the pSPB184 with XbaI and KpnI, so as to obtain pSPB1519A. A DNA fragment obtained by digestion of the pSPB1519A with AscI was inserted into the AscI site of pSPB1157 to obtain pSPB1519. The pSPB1519 was digested with AscI and inserted into the AscI site of pSPB1157 to obtain pSPB1519. The MaDES6 gene, MaDES5 gene, and MaELO gene were transcribed in the same direction on the plasmid pSPB1519, and were controlled by the same constitutive promoter.

(ii) Construction of *Marchantia polymorpha*-Derived Gene Vector (pSPB2368)

The pUCAP (van Engelen et al. Transgenic Research 4, 288-290, 1995) was digested with AscI, ligated to a SgfI linker. By further digesting it with PacI followed by ligation to a FseI linker, pUCSAPF was obtained. In the same manner, InpBINPLUS was processed to obtain pBINSAPF.

In addition, the pUC19 was digested with HindIII and ligated to a PacI linker. By further digesting it with EcoRI followed by ligation to a FseI linker, pUCPF was obtained as a subcloning vector. Further, the pUC19 was digested with HindIII and ligated to a SgfI linker. By further digesting it with EcoRI followed by ligation to an AscI linker, pUCSA was obtained. A vector in which E1235S was inserted into the HindIII-XbaI site of pUCSAPF, and in which a mannopin synthetase (mas) gene terminator was inserted into the SacI-EcoRI site of pUCSAPF was digested with XbaI and SacI and blunted to obtain pSPB2353A. To a blunt end of pSPB2353A, a DNA fragment containing the MpDES6 gene which was excised from the p35S-MpDES6 with XbaI and blunted was ligated. As a result, pSPB2353 was obtained.

A vector in which E1235S was inserted into the HindIII-XbaI site of pUCSA, and in which a mannopin synthetase (mas) gene terminator was inserted into the SacI-EcoRI of pUCSA was digested with XbaI and SacI to obtain pSPB2355A.

Meanwhile, using the p35S-MpELO1 as a template, PCR was carried out using the following primers:

```
XbaMpELOf:
                                    (SEQ ID NO: 43)
5'-AGTCTCTAGAGCGATGGAGGCGTACG-3';
and SacMpELOr:
                                    (SEQ ID NO: 44)
5'-CAGTGAGCTCGGTGTCTTATTCTGCC-3'.
```

PCR was run using a highly accurate KOD-plus-DNA polymerase (Toyobo) as an enzyme. The reaction was carried out at a maintained temperature of 94° C. for two minutes, followed by 25 cycles of reaction at 94° C. for 15 seconds and at 68° C. for 1 to 3 minutes. An MpELO1 DNA fragment so prepared was digested with XbaI and SacI, and was ligated to the pSPB2355A to obtain pSPB2355. Further, a DNA fragment obtained by the digestion of pSPB2355 with SgfI and AscI was ligated to pSPB2353 digested with SgfI and AscI. As a result, pSPB2361 was obtained.

A vector in which E1235S was inserted into the HindIII-XbaI site of pUCPF, and in which a mannopin synthetase (mas) gene terminator was inserted into the SacI-EcoRI site of pUCPF was digested with XbaI and SacI to obtain pSPB2352A.

Meanwhile, using the p35S-MpDES5 as a template, PCR was carried out using the following primers:

```
XbaMpD5f:
                                    (SEQ ID NO: 45)
5'-AGCTTCTAGAGCCATGCCGCCACACGCCC-3';
and SacMpD5r:
                                    (SEQ ID NO: 46)
5'-CAGTGAGCTCTCAGCCATCCAGTCGT-3'.
```

The PCR conditions were the same.

An MpD5 DNA fragment prepared by the PCR was digested with XbaI and SacI and ligated to pSPB2352A to obtain pSPB2352.

A DNA fragment obtained by the digestion of pBINSAPF with PacI and FseI was ligated to a DNA fragment containing the MpDES5 gene which was excised from pSPB2352 with PacI and FseI. As a result, pSPB2368A was obtained. Further, pSPB2368A was digested with SgfI and PacI and ligated to a DNA fragment containing the MpDES6 and MpELO1 genes which were excised from pSPB2361 with SgfI and PacI. As a result, pSPB2368 was obtained. The MpDES6 gene, MpDES5 gene, and MpELO1 gene were transcribed in the same direction on the plasmid pSPB2368, and were controlled by the same constitutive promoter.

(iii) Gene Introduction into Tobacco

Next, according to a known method (Plant J. 5, 81, 1994), *Agrobacterium tumefaciens* (strain: Ag10 (Lazo et al. 1991, Biotechnology 9: 963-967)) was transformed using pSPB2368 or pSPB1519. The transformed *Agrobacterium* having pSPB2368 or pSPB1519 was used to infect a tobacco leaf disk. From the transgenic tobacco leaf so obtained, RNA was extracted using a RNeasy Plant Mini Kit (Qiagen), and a line expressing the introduced gene was selected by RT-PCR using an ordinary method.

From the tobacco leaf that has incorporated the pSPB1519 containing the filamentous fungus-derived enzyme gene (pSPB1519-transformed tobacco), and from the tobacco leaf that has incorporated the pSPB2368 containing the *Marchantia polymorpha*-derived enzyme gene (pSPB2368-transformed tobacco), lipids were extracted according to known methods (Yasuhiko FUJINO, "Seibutsu-Kagaku Jikken-ho (Method of Biochemical Experiment) 9", Gakkai Shuppan Center (1978); Akihiro YAMADA, "Seibutsu-Kagaku Jikken-ho (Method of Biochemical Experiment) 24", Gakkai Shuppan Center (1989)). The lipids were analyzed by gas chromatography (Hewlett Packard, HP-6800). The result of analysis is shown in Table 1.

Note that, the same analysis was carried out using, as a control, a tobacco leaf into which no gene was introduced.

TABLE 1

|  | Control (%) | Control (mg/gFW) | pSPB2368 (%) | pSPB2368 (mg/gFW) | pSPB1519 (%) |
|---|---|---|---|---|---|
| Linoleic acid | 9.55 | 1.17 | 1.37 | 0.2 | 9.51 |
| α-linolenic acid | 49.99 | 6.12 | 17.83 | 2.58 | 39.24 |
| γ-linolenic acid | 0 | 0 | 4.06 | 0.59 | 3.37 |
| Dihomo-γ-linolenic acid | 0 | 0 | 10.85 | 1.57 | 3.09 |
| Arachidonic acid | 0 | 0 | 10.27 | 1.49 | 0 |
| Eicosatetraenoic acid | 0 | 0 | 4.89 | 0.71 | 0 |
| Eicosapentaenoic acid | 0 | 0 | 2.68 | 0.39 | 0 |
| Total amount of lipids | — | 12.25 | — | 14.48 | — |

In this Example, gas chromatography analysis was made under the following conditions:
(Gas Chromatography Analysis Condition)
Column: Supelco SP-2330, Fused Silica Capillary Column, 30 m×0.32 mm ID, 0.2 μm;
Temperature: Inj: 240° C., Det: 250° C., Oven: 180° C. for 3 min, 180° C.→220° C. (2° C./min); and
Column flow rate: 30 cm/sec, Pressure: 200 kPa, Detector: FID.

Each peak in the chromatogram was determined by a retention time of methyl ester of normal fatty acids and GC-MASS (Hewlett Packard, HP-5973) analysis, and the proportions of the respective fatty acids were determined in accordance with a peak area. In Table 1, "Control" indicates a control, "pSPB2368" indicates the pSPB2368-transformed tobacco, "pSPB1519" indicates the pSPB1519-transformed tobacco.

The results shown in Table 1 confirmed accumulation of dihomo-γ-linolenic acid in the tobacco that has incorporated the pSPB1519 containing the filamentous fungus-derived genes (pSPB1519-transformed tobacco), but no accumulation of arachidonic acid. On the other hand, in the tobacco that has incorporated the pSPB2368 containing the *Marchantia polymorpha*-derived enzyme genes (pSPB2368-transformed tobacco), accumulation of not only arachidonic acid but also eicosatetraenoic acid and eicosapentaenoic acid was confirmed. These results suggest that, in higher plants, the *Marchantia polymorpha*-derived enzymes are functionally superior to the filamentous fungus-derived enzymes in the ability to synthesize arachidonic acid and other polyunsaturated fatty acids using linoleic acid and α-linolenic acid as substrates.

Abbadi has reported that by introducing *Phaeodactylum tricornutum*-derived Δ6 desaturase and Δ5 desaturase, and a *Physcomitrella patens* chain elongase gene into tobacco and flax (*Linum usitatissimum*), 1.5% arachidonic acid was accumulated in a seed of tobacco, and 1.0% arachidonic acid was accumulated in a flax (Amine Abbadi et al. Plant Cell 16, 2734-2748, 2004).

In the present Example, by introducing each gene of *Marchantia polymorpha*-derived Δ6 desaturase, Δ5 desaturase, and chain elongase into tobacco, 10% or greater arachidonic acid was accumulated in a tobacco leaf. This result suggests that the pSPB2368-transformed tobacco in the present Example is capable of more efficiently synthesizing polyunsaturated fatty acids, as compared with the foregoing report.

Further, it has been reported that as a result of lipid modification of *Arabidopsis thaliana* using three types of genes: *Isochrysis galbana*-derived Δ9 chain elongase, *Englena gracilis*-derived Δ8 desaturase, and filamentous fungus-derived Δ5 desaturase, 6.6 mol % of arachidonic acid and 22.5 mol % of fatty acids having 20 or more carbon atoms with respect to the total lipids were contained in the leaf (Baoxiu Qi et al. Nature Biotechnology 22, 739-745, 2004). In this report, polyunsaturated fatty acids are synthesized through a modification pathway different from the pathway using the Δ6 desaturase, Δ5 desaturase, and chain elongase, and it was found that more polyunsaturated fatty acids could be accumulated when *Marchantia polymorpha*-derived enzymes were used, although a simple comparison cannot be made.

The pSPB2368-transformed tobacco having a 30% or greater modified fatty acid content with respect to the total lipids showed no morphological abnormalities. Further, since the pSPB2368-transformed tobacco has no problem in terms of fertility and bore a lot of seeds, it is believed that the ectopical increase of the polyunsaturated fatty acids has no significant effect on the growth and development of plants.

In the transgenic plants reported so far, up to about 20% of total lipids is polyunsaturated fatty acids having 20 or more carbon atoms. The value reduces to about 6% when only arachidonic acid is considered. However, as in the present Example, the use of *Marchantia polymorpha*-derived fatty acid synthetases makes it possible to go beyond this limitation and produce more polyunsaturated fatty acids in plants.

Specific embodiments or examples implemented in the best mode for carrying out the invention only show technical features of the present invention and are not intended to limit the scope of the invention. Variations can be effected within the spirit of the present invention and the scope of the following claims.

Industrial Applicability

The present invention provides a Δ5 desaturase gene, a Δ6 desaturase gene, and a Δ6 chain elongase gene, which are obtained from a single species of Marchantiales. The three genes, when expressed together in a plant, function more desirably in the plant as compared with the case where genes obtained from organisms of different species are expressed. Further, since Marchantiales can be considered as a model plant of higher plants, the genes derived from Marchantiales can function more desirably in plants than genes derived from non-plants.

Further, with a transformant according to the present invention, polyunsaturated fatty acids such as arachidonic acid or eicosapentaenoic acid (EPA) can be produced. More advantageously, a transformant according to the present invention produces these fatty acids at low cost by an environmentally friendly process. The product arachidonic acid or EPA can be inexpensively marketed as a material with different purposes. When used as food, the transformant can increase the value of the product with its high arachidonic acid or EPA content.

As described above, genes and proteins of the present invention are useful in producing arachidonic acid and EPA. Further, transformants that have incorporated genes of the present invention are highly useful in the arachidonic acid or EPA production in pharmaceutical industry, food industry, and various other material industries. The usefulness of the transformant is particularly notable in agricultures when the transformant is a plant, because the transformation increases arachidonic acid and EPA levels in plants.

The invention claimed is:

1. An isolated Marchantiales-derived nucleic acid-having at least 90% identity to the nucleotide sequence of SEQ ID NO: 5 or the complementary sequence thereto, wherein said gene encodes a protein having Δ5 fatty acid desaturating activity.

2. The isolated nucleic acid of claim 1, wherein said nucleic acid consists of the nucleotide sequence of SEQ ID NO: 5.

3. The isolated nucleic acid of claim 1, wherein said nucleic acid consists of the nucleotide sequence of nucleotides 375 to 1829 of SEQ ID NO: 5.

4. The isolated nucleic acid of claim 1, wherein the nucleic acid encodes a protein having the amino acid sequence of SEQ ID NO: 6, or having the amino acid sequence that has been modified by substitution, deletion, insertion, and/or addition of one to ten amino acids of SEQ ID NO: 6.

5. A recombinant expression vector comprising the isolated nucleic acid of claim 1.

6. A transformed cell comprising the recombinant expression vector of claim 5.

7. A plant, a progeny of said plant, a vegetatively propagated plant of said plant, or a tissue of said plant, wherein the isolated nucleic acid of claim 1 is expressed in the plant, the progeny of said plant, the vegetatively propagated plant of said plant, or the tissue of said plant.

8. The plant, the progeny of said plant, the vegetatively propagated plant of said plant, or the tissue of said plant of claim 7, wherein said plant, the progeny of said plant, the vegetatively propagated plant of said plant, or the tissue of said plant has a modified fatty acid composition.

9. A method of producing fatty acids comprising growing the plant of claim 7, and obtaining said fatty acids from said plant or plant tissue.

10. A method of modifying a fatty acid composition comprising expressing the isolated nucleic acid of claim 1 in a plant.

* * * * *